US007723123B1

(12) United States Patent
Murphy et al.

(10) Patent No.: US 7,723,123 B1
(45) Date of Patent: May 25, 2010

(54) WESTERN BLOT BY INCORPORATING AN AFFINITY PURIFICATION ZONE

(75) Inventors: Matthew B. Murphy, San Francisco, CA (US); Robert S. Dubrow, San Carlos, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 1914 days.

(21) Appl. No.: 10/159,605

(22) Filed: May 31, 2002

Related U.S. Application Data

(60) Provisional application No. 60/296,139, filed on Jun. 5, 2001.

(51) Int. Cl.
G01N 33/558 (2006.01)
(52) U.S. Cl. .................................................. 436/514
(58) Field of Classification Search .................. 435/4; 436/514, 517, 518, 523, 524–535, 544–546; 535/4–7.1, 7.91–7.95, 283.1, 287.1, 287.2, 535/287.3, 288.4, 288.5, 288.6, 288.7
See application file for complete search history.

(56) References Cited

U.S. PATENT DOCUMENTS

| | | | |
|---|---|---|---|
| 4,390,403 A | | 6/1983 | Batchelder |
| 4,425,438 A | * | 1/1984 | Bauman et al. ............. 436/527 |
| 4,908,112 A | | 3/1990 | Pace |
| 5,037,544 A | * | 8/1991 | Snyder ..................... 210/198.2 |
| 5,126,022 A | | 6/1992 | Soane et al. |
| 5,271,724 A | | 12/1993 | van Lintel |
| 5,277,556 A | | 1/1994 | van Lintel |
| 5,316,926 A | * | 5/1994 | Brown et al. ................ 435/101 |
| 5,375,979 A | | 12/1994 | Trah |
| 5,498,392 A | | 3/1996 | Wilding et al. |
| 5,571,410 A | | 11/1996 | Swedberg et al. |
| 5,585,069 A | | 12/1996 | Zanzucchi et al. |
| 5,587,128 A | | 12/1996 | Wilding et al. |
| 5,593,838 A | | 1/1997 | Zanzucchi et al. |
| 5,603,351 A | | 2/1997 | Cherukuri et al. |
| 5,616,502 A | | 4/1997 | Haugland et al. |
| 5,635,358 A | | 6/1997 | Wilding et al. |
| 5,637,469 A | | 6/1997 | Wilding et al. |
| 5,699,157 A | | 12/1997 | Parce |
| 5,716,852 A | | 2/1998 | Yager et al. |
| 5,750,015 A | | 5/1998 | Soane et al. |
| 5,779,868 A | | 7/1998 | Parce et al. |
| 5,800,690 A | | 9/1998 | Chow et al. |
| 5,804,384 A | | 9/1998 | Muller et al. |
| 5,842,787 A | | 12/1998 | Kopf-Sill et al. |
| 5,852,495 A | | 12/1998 | Parce |
| 5,858,187 A | | 1/1999 | Ramsey et al. |
| 5,858,195 A | | 1/1999 | Ramsey |
| 5,869,004 A | | 2/1999 | Parce et al. |
| 5,876,675 A | | 3/1999 | Kennedy |
| 5,880,071 A | | 3/1999 | Parce et al. |
| 5,882,465 A | | 3/1999 | McReynolds |
| 5,885,470 A | | 3/1999 | Parce et al. |
| 5,919,523 A | | 7/1999 | Sundberg et al. |
| 5,932,100 A | | 8/1999 | Yager et al. |
| 5,942,443 A | | 8/1999 | Parce et al. |
| 5,948,227 A | | 9/1999 | Dubrow |
| 5,952,173 A | | 9/1999 | Hansmann et al. |
| 5,955,028 A | | 9/1999 | Chow |
| 5,957,579 A | | 9/1999 | Kopf-Sill et al. |
| 5,958,203 A | | 9/1999 | Parce et al. |
| 5,958,694 A | | 9/1999 | Nikiforov |
| 5,959,291 A | | 9/1999 | Jensen |
| 5,964,995 A | | 10/1999 | Nikiforov et al. |
| 5,965,001 A | | 10/1999 | Chow et al. |
| 5,965,410 A | | 10/1999 | Chow et al. |
| 5,972,187 A | | 10/1999 | Parce et al. |
| 5,976,336 A | | 11/1999 | Dubrow et al. |
| 5,989,402 A | | 11/1999 | Chow et al. |
| 6,001,229 A | | 12/1999 | Ramsey |
| 6,001,231 A | | 12/1999 | Kopf-Sill |
| 6,004,515 A | | 12/1999 | Parce et al. |
| 6,011,252 A | | 1/2000 | Jensen |
| 6,012,902 A | | 1/2000 | Parce |
| 6,042,709 A | | 3/2000 | Parce et al. |
| 6,042,710 A | | 3/2000 | Dubrow |
| 6,046,056 A | | 4/2000 | Parce et al. |
| 6,062,261 A | | 5/2000 | Jacobson et al. |
| 6,068,752 A | | 5/2000 | Dubrow et al. |
| 6,071,478 A | | 6/2000 | Chow |

(Continued)

FOREIGN PATENT DOCUMENTS

WO  WO 94/05414  3/1994

(Continued)

OTHER PUBLICATIONS

Bousse et al., "Protein Sizing on a Microchip", Analytical Chemistry, vol. 73, No. 6, pp. 1207-1212, Mar. 15, 2001.*

(Continued)

Primary Examiner—Ann Y Lam

(57) ABSTRACT

An upstream affinity purification region is used to bind one or more component of interest in a mixture of components prior to separating the mixture of components. Detection of the separated components and a released component of interest provide identification of the component of interest. In addition, post separation dilution is optionally used to improve detection of the mixture of components and the released component of interest. Microfluidic devices and systems suitable for performing such analyses are also provided.

40 Claims, 3 Drawing Sheets

U.S. PATENT DOCUMENTS

| | | | |
|---|---|---|---|
| 6,074,725 | A | 6/2000 | Kennedy |
| 6,080,295 | A | 6/2000 | Parce et al. |
| 6,090,252 | A * | 7/2000 | Bjellqvist ................... 204/468 |
| 6,100,541 | A | 8/2000 | Nagle et al. |
| 6,120,666 | A | 9/2000 | Jacobson et al. |
| 6,174,675 | B1 | 1/2001 | Chow et al. |
| 6,221,226 | B1 | 4/2001 | Kopf-Sill |
| 6,225,047 | B1 * | 5/2001 | Hutchens et al. ............... 435/5 |
| 6,235,471 | B1 | 5/2001 | Knapp et al. |
| 6,280,589 | B1 | 8/2001 | Manz et al. |
| 6,280,618 | B2 | 8/2001 | Watkins et al. |
| 6,306,590 | B1 | 10/2001 | Mehta |
| 6,344,326 | B1 * | 2/2002 | Nelson et al. .................. 435/6 |
| 6,416,642 | B1 | 7/2002 | Alajoki et al. |

FOREIGN PATENT DOCUMENTS

| | | |
|---|---|---|
| WO | WO 96/04547 | 2/1996 |
| WO | WO 97/02357 | 1/1997 |
| WO | WO 98/00231 | 1/1998 |
| WO | WO 98/00705 | 1/1998 |
| WO | WO 98/00707 | 1/1998 |
| WO | WO 98/02728 | 1/1998 |
| WO | WO 98/05424 | 2/1998 |
| WO | WO 98/22811 | 5/1998 |
| WO | WO 98/45481 | 10/1998 |
| WO | WO 98/45929 | 10/1998 |
| WO | WO 98/46438 | 10/1998 |
| WO | WO 98/49548 | 11/1998 |
| WO | WO 98/55852 | 12/1998 |
| WO | WO 98/56956 | 12/1998 |
| WO | WO 99/00649 | 1/1999 |
| WO | WO 99/10735 | 3/1999 |
| WO | WO 99/12016 | 3/1999 |
| WO | WO 99/16162 | 4/1999 |
| WO | WO 99/19056 | 4/1999 |
| WO | WO 99/19516 | 4/1999 |
| WO | WO 99/29497 | 6/1999 |
| WO | WO 99/56954 | 11/1999 |
| WO | WO 99/64848 | 12/1999 |
| WO | WO 00/09753 | 2/2000 |
| WO | WO 00/46594 | 8/2000 |
| WO | WO 00/50172 | 8/2000 |
| WO | WO 00/50642 | 8/2000 |
| WO | WO 01/14064 | 3/2001 |

OTHER PUBLICATIONS

Cohen, C.B. et al., "A Microchip-Based Enzyme Assay for Protein Kinase A," *Anal. Chem.* (1999) 273:89-87.

Dasgupta, P.K. et al., "Electroosmosis: A Reliable Fluid Propulsion System for Flow Injection Analysis," *Anal. Chem.* (1994) 66:1792-1798.

Effenhauser, C.S. et al., "Glass Chips for High-Speed Capillary Electrophoresis Separations with Submicrometer Plate Heights," *Anal. Chem.* (1993) 65: 2637-2642.

Effenhauser, C.S. et al., "High Speed Separation of Anitsense Oligonucleotides on a Micromachined Capillary Electrophoresis Device," *Anal. Chem.* (1994) 66: 2949-2953.

Effenhauser, C.S. et al., "Integrated Capillary Electrophoresis on Flexible Silicone Microdevices: Analysis of DNA Restriction Fragments and Detection of Single DNA Molecules on Microchips," *Anal. Chem.* (1997) 69: 3451-3457.

Fan, Z.H. et al., "Micromachining of Capillary Electrophoresis Injectors and Separators on Glass Chips and Evaluation of Flow at Capillary Intersections," *Anal. Chem.* (1994) 66: 177-184.

Fister, J.C. III et al., "Counting Single Chromophore Molecules for Ultrasensitive Analysis and Separations on Microchip Devices," *Anal. Chem.* (1998) 70: 431-437.

Hadd, A.G. et al., "Microfluidic Assays of Acetylcholinesterase," *Anal. Chem.* (1999) 71: 5206-5212.

Harrison, J. et al., "Capillary Electrophoresis and Sample Injection Systems Integrated on a Planar Glass Chip," *Anal. Chem.* (1992) 64: 1926-1932.

Harrison, J. et al., "Towards Miniaturized Electrophoresis and Chemical Analysis Systems on Silicon: An Alternative to Chemical Sensors," *Sensors and Actuators B* (1993) 10: 107-116.

Harrison, J. et al., "Micromachining a Miniaturized Capillary Electrophoresis-Based Chemical Analysis System on a Chip," *Science* (1993) 261: 895-897.

Harrison, D.J. et al., "Integrated Electrophoresis Systems for Biochemical Analyses," *Solid-State Sensor and Actuator Workshop* (1994) 21-24.

Helenius, et al., "Biomembranes," *Methods in Enzymoloοy* (1979) 56(63):734-749.

Huse, et al., "Generation of a Large Combinatorial Library of the Immunoglobulin Repertoire in Phage Lambda," *Science* (1989) 246:1275-1281.

Jacobson, S.C. et al., "Effects of Injection Schemes and Column Geometry on the Performance of Microchip Electrophoresis Devices," *Anal. Chem.* (1994) 66:1107-1113.

Jacobson, S.C. et al., "High-Speed Separations on a Microchip," *Anal. Chem.* (1994) 66: 1114-1118.

Jacobson, S.C. et al., "Open Channel Electrochromatography on a Microchip," *Anal. Chem.* (1994) 66: 2369-2373.

Jacobson, S.C. et al., "Precolumn Reactions with Electrophoretic Analysis Integrated on a Microchip," *Anal. Chem.* (1994) 66: 4127-4132.

Jacobson, S.C. et al., "Microchip Electrophoresis with Sample Stacking," *Electrophoresis* (1995) 16: 481-486.

Jacobson, S.C. et al., "Fused Quartz Substrates for Microchip Electrophoresis " *Anal. Chem.* (1995) 67: 2059-2063.

Jacobson, S.C. et al., "Integrated Microdevice for DNA Restriction Fragment Analysis," *Anal. Chem.* (1996) 68: 720-723.

Jacobson, S.C. et al., "Electrokinetic Focusing in Microfabricated Channel Structures," *Anal. Chem.* (1997) 69: 3212-3217.

Jacobson, S.C. et al., "Microfluidic Devices for Electrokinetically Driven Parallel and Serial Mixing," *Anal. Chem.* (1999) 71: 4455-4459.

Manz, A. et al., "Miniaturized Total Chemical Analysis Systems: a Novel Concept for Chemical Sensing," *Sensors and Actuators* (1990) B1: 244-248.

Manz, A. et al., "Micromachining of Monocrystalline Silicon and Glass for Chemical Analysis Systems," *Trends in Analytical Chemistry* (1991) 10:144-149.

Manz, A. et al., "Planar Chips Technology for Miniaturization and Integration of Separation Techniques into Monitoring Systems," *Journal of Chromatography* (1992) 593:253-258.

Manz, A. et al., "Electroosmotic Pumping and Electrophoretic Separations for Miniaturized Chemical Analysis Systems," J. Micromach. Microeng. (1994) 4: 257-265.

Manz, A. et al., "Parallel Capillaries for High Throughput in Electrophoretic Separations and Electroosmotic Drug Discovery Systems," International Conference on Solid-State Sensors and Actuators (1997) 915-918.

McCormick, R.M. et al., "Microchannel Electrophoretic Separations of DNA in Injection-Molded Plastic Substrates," *Anal. Chem.* (1997) 69: 2626-2630.

Moore, A.W. et al., "Microchip Separations of Neutral Species via Micellar Electrokinetic Capillary Chromatography," *Anal. Chem.* (1995) 67: 4184-4189.

Ramsey, J.M. et al., "Microfabricated Chemical Measurement Systems " *Nature Medicine* (1995) 1:1093-1096.

Salimi-Moosavi, H. et al., "Biology Lab-on-a-Chip for Drug Screening," Solid-State Sensor and Actuator Workshop (1998) 350-353.

Seiler, K. et al., "Planar Glass Chips for Capillary Electrophoresis: Repetitive Sample Injection, Quantitation, and Separation Efficiency," *Anal. Chem.* (1993) 65:1481-1488.

Seiler, K. et al., "Electroosmotic Pumping and Valveless Control of Fluid Flow within a Manifold of Capillaries on a Glass Chip," *Anal. Chem.* (1994) 66:3485-3491.

Sundberg, S.A., "High-Throughput and Ultra-High-Throughput Screening: Solution-and Cell-Based Approaches," *Current Opinions in Biotechnology* 2000, 11:47-53.

Ueda, M. et al., "Imaging of a Band for DNA Fragment Migrating in Microchannel on Integrated Microchip," *Materials Science and Engineering C* (2000) 12:33-36.

Wang, C. et al., "Integration of Immobilized Trypsin Bead Beds for Protein Degestion within a Microfluidic Chip Incorporating Capillary Electrophoresis Separations and an Electrospray Mass Spectrometry Interface," *Rapid Commin. Mass Spectrom.* (2000) 14:1377-1383.

Ward, E. S. et al., "Binding Activities of a Repertoire of Single Immunoglobin Variable Domains Secreted from *Escherichia coli*," *Nature* (1989) 341: 544-546.

Woolley, A.T. et al., "Ultra-High-Speed DNA Fragment Separations Using Microfabricated Capillary Array Electrophoresis Chips," *Proc. Natl. Acad. Sci. USA* (1994) 91:11348-11352.

Woolley, A.T. et al., "Functional Integration of PCR Amplification and Capillary Electrophoresis in a Microfabricated DNA Analysis Device," Anal. Chem. (1996) 68: 4081-4086.

Woolley, A.T. et al., "High-Speed DNA Genotyping Using Microfabricated Capillary Array Electrophoresis Chips," *Anal. Chem.* (1997) 69:2181-2186.

Woolley, A.T. et al., "Capillary Electrophoresis Chips with Integrated Electrochemical Detection," *Anal. Chem.* (1998) 70: 684-688.

Zhang, B. et al., "Microfabricated Devices for Capillary Electrophoresis-Electrospray Mass Spectrometry," *Anal. Chem.* (1999) 71:3258-3264.

* cited by examiner

WESTERN BLOT BY INCORPORATING AN AFFINITY PURIFICATION ZONE

CROSS-REFERENCE TO RELATED APPLICATION

This application claims the benefit of U.S. Provisional Patent Application No. 60/296,139 filed Jun. 5, 2001, which is incorporated herein by reference in its entirety for all purposes.

BACKGROUND OF THE INVENTION

Analytic detection of biomolecules, e.g., proteins, nucleic acids, and the like, is fundamental to molecular biology. In many applications, it is desirable to detect the presence of one or more particular molecules in a sample. For example, identification of a particular DNA sequence within a mixture of restriction fragments is used to determine the presence, position, and number of copies of a gene in a genome. It is also an integral technique in DNA typing. Analytic detection is also used, e.g., in disease diagnosis and drug development, to determine the presence of a particular antibody or protein, e.g., in a blood sample or large chemical library. Detection of biomolecules is therefore of fundamental value in, e.g., diagnostic medicine, archaeology, anthropology, modern criminal investigation, and the like. To meet these needs many techniques, e.g., DNA blotting, RNA blotting, protein blotting, and ELISA assays, have been developed to detect the presence of a particular molecule or fragment in the midst of a complex sample containing similar molecules.

For example, western blotting is useful for detecting one or more specific proteins in a complex protein mixture, such as a cell extract. The procedure involves fractionating the protein mixture, typically by denaturing polyacrylamide gel electrophoresis, and transferring and immobilizing the mixture onto a solid membrane of nitrocellulose or nylon by electroblotting. The loaded membrane is then incubated with an antibody raised against the protein of interest. The antibody-antigen complex formed on the membrane is then detected by a procedure that typically involves the application of a second antibody, raised against the first antibody, and to which an enzyme has been covalently linked. The insoluble reaction product generated by the enzyme action can then be used to indicate the position of the target protein on the membrane. The sensitivity of detection can be increased by amplification of the signal using either the biotin-streptavidin system or by chemiluminescence detection.

This classical procedure is very time consuming and labor intensive. For example, transferring the proteins to a membrane is generally a time consuming step and is typically done by capillary blotting or by the faster and more efficient methods of vacuum blotting or electrophoretic blotting.

More recently, new and faster microfluidic methods of performing biological assays in microfluidic systems have been developed, such as those described by the pioneering applications of Parce et al., "High Throughput Screening Assay Systems in Microscale Fluidic Devices" WO 98/00231 and in Knapp et al., "Closed Loop Biochemical Analyzers" (WO 98/45481; PCT/US98/06723). For example, high throughput methods for analyzing biological reagents, including proteins, are described in these applications.

Improved methods for performing western blot and affinity assays are, accordingly desirable, particularly those which take advantage of high-throughput, low cost microfluidic systems. The present invention provides these and other features by providing high throughput microscale systems for analyte detection, affinity purification, western blots, and the like, and many other features that will be apparent upon complete review of the following disclosure.

SUMMARY OF THE INVENTION

The present invention provides methods, devices, and systems for detecting one or more component of interest in a complex mixture, e.g., in a microfluidic system. Typically, the method involves incorporation of an affinity purification zone upstream from a separation region in a microfluidic device. For example, a mixture of proteins containing a protein of interest is flowed through an affinity purification zone or binding region, in which at least a portion of the component of interest specifically binds to a protein binding moiety, e.g., an antibody. The mixture of proteins, e.g., the unbound proteins, is then flowed through a separation region to observe all protein bands. The affinity bound protein of interest is then released from the affinity purification zone and flowed through the separation region, e.g., to observe a single protein band corresponding to the component of interest. Detecting the components as they elute from the separation region and overlaying the data for the mixture of components with the data for the released protein of interest yields a western-blot style readout for identifying the protein of interest.

In one aspect, a method for detecting a component of interest in a microfluidic system is provided. The method typically comprises flowing a mixture of components comprising a component of interest through a binding channel region or affinity purification zone, in which at least a portion of the component of interest binds to a component-binding moiety. Flowing the mixture of components through the binding channel region optionally comprises applying pressure to the mixture of components in the binding channel region or electrokinetically flowing the mixture of components.

The binding channel region typically comprises the component-binding moiety and is upstream from a separation channel region. In some embodiments, the binding channel region is a derivatized channel or channel region. The binding channel region optionally comprises one or more particle set comprising a plurality of particle member types, e.g., particle member types comprising a component binding moiety. The particle member types, which are typically about 0.1 μm to about 50 μm in diameter, optionally comprise a polymeric material, a silica material, a ceramic material, a glass material, a magnetic material, a metallic material, an organic material, or the like. Example materials include, but are not limited to, PVDF, polyamide, nylon, nitrocellulose, and the like. Binding a component binding moiety to a particle set optionally comprises adsorbing the component binding moiety onto one or more members of such a particle set. The component of interest then binds to the particle set via specific binding with the component binding moiety.

In some embodiments of the present invention, the component of interest comprises a protein and the component-binding moiety comprises a protein-binding moiety. For example, the component-binding moiety optionally comprises an antibody specific to the component of interest. In other embodiments, the component of interest comprises a carbohydrate and the component-binding moiety comprises a carbohydrate-binding moiety, e.g., a lectin specific to a carbohydrate of interest. In addition, the component-binding moiety and/or the component of interest optionally comprises a label moiety.

After the component of interest, or at least a portion thereof, is bound in the binding region, the mixture of components is typically flowed through a separation channel region, e.g., electrokinetically, resulting in one or more separated components. The mixture of components is typically electrophoretically separated in a polymer or gel disposed within the separation channel region. For example, the method typically comprises electrophoretically separating a mixture of components in a polyacrylamide solution, matrix, or gel disposed within the separation channel region. In some embodiments, the mixture of components is contacted with a detergent, e.g., SDS, and heated, e.g., using joule heating, prior to separation. The heating and detergent are typically applied after the mixture has been flowed through the binding channel region. As they are separated or as they elute from the separation region, the mixture of components is also typically detected.

The component of interest is then released, e.g., after the mixture has been separated, from the component-binding moiety, thereby resulting in a released component of interest. Release of the component of interest from the component binding moiety or particle is optionally achieved, e.g., by adjusting the temperature or pH in the binding channel region or by, e.g., introducing one or more releasing reagent into the binding channel region.

The released component of interest is then flowed through the separation region, e.g., electrokinetically. Typically, the method comprises contacting the released component of interest with a detergent, e.g., SDS and heating it, e.g., by joule heating, prior to flowing the released component through the separation region, e.g., for detection and identification.

The one or more separated components and/or the released component of interest is optionally detected, e.g., through optical detection using a label moiety. For example, a luminescent, color, or fluorescent label moiety fixed to one or more of the separated components or the released component of interest is optionally optically detected. In some embodiments, the method further comprises labeling the mixture of components with a fluorescent label, e.g., in a microfluidic channel, and detecting the separated components or the released component of interest by detecting the fluorescent label, e.g., in a detection channel region.

In some embodiments, the separated components are detected using a dye, e.g., a lipophilic dye, that associates with the separated components, allowing their detection. The released component of interest is also optionally detected in this manner. For example, the mixture of components is optionally separated in a separation region which comprises a separation buffer comprising such a dye. In addition, the buffer optionally includes a detergent, which buffer is diluted prior to detection, e.g., such that the detergent is diluted to a concentration below the critical micelle concentration for the detergent, e.g., in the separation buffer. The separated components are typically flowed through a dilution region prior to detection, e.g., a portion of a diluent is mixed with the separated components prior to detection, e.g., providing improved detection. The released component of interest is also optionally similarly treated, e.g., diluted post separation and prior to detection.

Typically, detecting the one or more separated components produces a first signal or a first data set and detecting the released component of interest produces a second signal or a second data set. The method further comprises deconvoluting the first signal and the second signal or the first data set and the second data set to identify the separated components and the component of interest. For example, deconvolution optionally comprises superimposing the first data set and the second data set to identify the component of interest. Alternatively, the released component of interest is identified by its migration time through the separation channel region. In other aspects, the molecular weight of the separated components and/or the released component of interest is determined, e.g., by determining the retention time of the separated components and/or the released component of interest in the separation channel region.

In another aspect, the present invention provides microfluidic devices and systems for detecting a component of interest in a mixture of components. Typical components of interest are identified above. A typical device comprises a body structure with a plurality of microscale channels disposed therein. The plurality of microscale channels typically comprises a separation channel region for separating the mixture of components and a binding region.

The binding region is typically upstream from, and fluidly connected to, the separation channel region. In addition, the binding region comprises a component-binding moiety, e.g., as described above, for binding a component of interest to the component-binding moiety prior to separating the mixture of components, e.g., in the separation channel region. The binding region optionally comprises a derivatized channel, e.g., comprising the component-binding moiety. In other embodiments, the binding region comprises a particle set comprising a plurality of particle member types as described above. The particles in this embodiment typically comprise the component-binding moiety.

A control system is typically operably coupled to the body structure, for directing the flow of, e.g., reagents, components, etc. through the device. Typically, the control system directs the flow of components through the device. For example, the mixture of components is directed to flow through the binding region, thereby binding a component of interest to a component binding moiety in the binding region. At least a portion of the component of interest becomes a bound component of interest, i.e., remaining in the binding region.

In addition, the control system directs the flow of the mixture of components through the separation channel region after flowing the mixture of components through the binding region. At least a portion of the component of interest, e.g., an unbound portion, typically remains in the mixture of components. The mixture of components is typically electrokinetically flowed through the separation channel region, resulting in one or more separated components. For example, the separation channel region optionally comprises a polyacrylamide gel filled region in which components are electrophoretically separated.

The control system also typically directs release of the bound component of interest from the binding channel, resulting in a released component of interest and flow of the released component of interest through the separation channel region.

In some embodiments, the devices optionally comprise a fluid direction system fluidly coupled to the body structure and operably coupled to the control system. The fluid direction system transports, e.g., the mixture of components, the component of interest, and/or the released component of interest through the microscale channels as directed by the control system. Example fluid direction systems comprise an electrokinetic based fluid direction system and/or a pressure based fluid direction system. For example, the mixture of components is optionally flowed through the binding region by the application of pressure from a pressure based fluid direction system and flowed through the separation channel electrophoretically using an electrokinetic based fluid direction system.

In another embodiment, the plurality of microscale channels in the devices of the present invention optionally comprises a heating zone positioned between the binding region and the separation channel region for heating various components, e.g., the mixture of components or the released component of interest. A temperature control element is typically operably coupled to the heating zone in this embodiment for heating the mixture of components or the released component of interest in the heating zone.

The devices also optionally comprise one or more sipper capillary fluidly connected to the binding region and upstream from the binding region. A source of the mixture of components is typically fluidly connected to the binding region, e.g., via the one or more capillary, for introducing samples into the devices.

An injection channel is also optionally included in the devices of the present invention. The injection channel is typically fluidly connected to the binding region and the separation channel region and is used for transferring the mixture of components or the released component of interest from the binding region to the separation channel region.

Dilution channels and/or regions are also optionally included in the devices of the invention to dilute materials, e.g., to dilute the detergent in a separation buffer to improve later detection. Such dilution channels typically intersect a downstream region of a separation channel upstream from the detection region. In some embodiments, the dilution channel intersects the detection region.

In other embodiments, the devices include a detection region downstream of the separation channel region. A detection system, e.g., a chemiluminescent, fluorescent, or colorimetric detector, is typically positioned proximal to such a detection region for detecting the mixture of components and the released component of interest, e.g., as they elute from the separation region.

In other embodiments, the devices of the present invention optionally include a computer operably coupled to the device and software for analyzing one or more signals produced by a detection system. For example, the detection system is optionally used to detect one or more separated components, resulting in a first data set. In addition, the detection system typically detects the released component of interest, resulting in a second data set.

Software, e.g., included with the computer, typically comprises at least a first instruction set for deconvoluting the first data set and the second data set to identify the separated components or the released component of interest. Deconvoluting typically comprises determining the retention time of one or more of the separated components or the released component of interest. In other embodiments, deconvoluting comprises superimposing or comparing the first data set and the second data set to identify the released component of interest.

DETAILED DISCUSSION OF THE INVENTION

Figure 1:
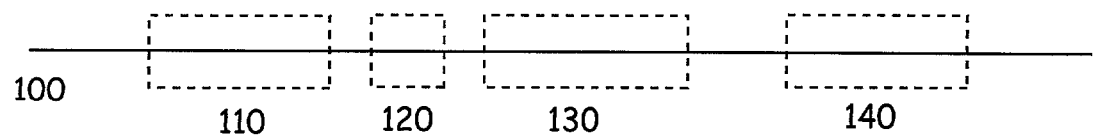
FIG. 1: Schematic of an example channel of the invention in which the binding region and the separation region comprises a single channel.

The present invention provides new technology for detecting a component of interest in a complex mixture. For example, the new technology optionally replaces the standard western blot assay. Standard western blotting technology involves separation of a mixture of components and then a time-consuming blotting procedure to detect the protein of interest from the mixture. The present invention provides methods and microscale devices for continuous flow binding, separation and detection. A time-consuming blotting step is not required, thus providing dramatically increased throughput as compared with prior art methods.

The present methods provide for separation of a mixture of components in a microfluidic separation channel or region. Prior to separation, the mixture of components is flowed through a binding channel or affinity purification zone in which it is contacted by a moiety that specifically binds the one or more component of interest within the mixture. For example the component of interest is optionally a protein that is detected by a binding reaction with an antibody specific to the protein. The component of interest is released from the binding channel and flowed through the separation channel region after the mixture of components. Components are detected as they elute from the separation channel and a comparison of data sets for the separated components from the mixture and the released component of interest allows identification of the component of interest.

The component of interest is detected in the present invention by binding the component of interest to a binding moiety that is specific to the component of interest. The component of interest is optionally a protein, nucleic acid, carbohydrate, or the like. In addition, the component of interest optionally includes biotin or avidin. The component is typically included in a complex mixture of various components, e.g., other proteins, nucleic acids, and the like. For example, the component of interest is optionally a component of a cell extract or serum sample.

In a preferred embodiment, such as in an assay analogous to a western assay or a western style assay, the component of interest is a protein. A "protein," as used herein, refers to a polymer of amino acid residues. The term applies to amino acid polymers in which one or more amino acid residue is an analog or mimetic of a corresponding naturally occurring amino acid or in which one or more amino acid residue is a modified naturally occurring amino acid residue (e.g., modified with the addition of, e.g., chemical groups such as methyl groups), as well as to naturally occurring amino acid polymers. A protein of biological or other interest is optionally detected using the methods, devices, and systems of the present invention.

For example, a "western" analysis (this term is used herein to refer to an antibody-protein binding analysis) is used to detect a specific protein of interest in a complex mixture of components, such as a cell extract. The procedure involves fractionating the protein mixture by electrophoresis and binding the protein of interest to an antibody specific to that protein. The methods of the present invention are applicable to other analytic detection assays as well, e.g., detection of nucleic acids or carbohydrates. For example, a carbohydrate of interest is optionally detected using the methods, devices, and systems of the present invention by providing a lectin as the component-binding moiety to bind a carbohydrate of interest.

In one embodiment of the present invention, a mixture of components, e.g., proteins, is flowed through a binding region and then separated in a microfluidic separation channel. The mixture of components comprising the component of interest, e.g., a protein of interest, is flowed through a binding channel region, which is upstream from a separation channel region. The binding channel region comprises a component-binding moiety which binds at least a portion of the component of interest, resulting in a bound component of interest. The mixture of components is then flowed through a separation channel or channel region and the bound component of interest remains in the binding channel region. As the mixture of components is flowed through the separation channel region, one or more separated components are produced and typically detected. The bound component of interest is then released and flowed through the separation channel region. The released component is also detected.

The mixture of components is optionally labeled to allow detection of the separated components and the released component of interest or an associative dye is added to the mixture of components and released component of interest prior to flowing them through the separation channel. The associative dye, which is typically included in the separation buffer, is picked up by the components as they flow through the separation channel. Alternatively, the dye is added prior to flowing the components through the separation channel. The associative dye, typically a lipophilic dye, is then detected, thereby detecting the components with which it is associated.

In one embodiment, an associative dye is used to detect the components and a post-separation dilution step is also performed to increase the efficiency of the detection. Typically, a detergent is added to the fluidic stream prior to separation to aid separation. Alternatively, the detergent is included in the separation buffer. The dye molecules that are used to detect the separated components and the component of interest also bind to detergent micelles, which form above a certain concentration of detergent. Therefore, a post-separation dilution of the separation buffer results in a dilution of the detergent below the critical micelle concentration and the dye no longer binds to the detergent molecules. Therefore, interfering background signals are avoided in the detection of the separated components and the component of interest.

In addition, the present invention provides microfluidic devices and systems for use in detecting a component of interest by the above methods. These systems and methods are described below.

I. Microfluidic Systems

The microfluidic devices of the present invention are used to detect the presence of a particular component of interest, e.g., a protein of interest. The devices generally comprise a body structure with a plurality of microscale channels fabricated therein. For example, the present system comprises one or more of: a separation channel or channel region, a binding channel or channel region or an affinity purification zone, a detection region, a heating zone, a dilution channel, and the like. The channels are fluidly coupled to each other and to various reservoirs or other sources of materials. In addition, a device of the invention typically includes a control system operably coupled to the body structure for directing the flow of materials through the plurality of channels. Materials used in the present invention include, but are not limited to, buffers, e.g., separation buffers or binding buffers, washing solutions, detergents, dyes, one or more sample comprising a mixture of proteins, a particle set, e.g., comprising a component binding moiety such as an antibody, and the like.

For example, the control system typically directs the flow of a mixture of components through a binding region and then into a separation region. In the binding region, a component of interest in the mixture of components is bound to a component-binding moiety. The remaining components in the mixture are directed to flow through a separation channel or channel region, resulting in separated components. The separated components are then typically directed to flow through a detection region for detection. The control system also directs release of the bound component of interest, upon which release, the control system directs the released component of interest to flow through the separation channel region and detection region for detection also.

The devices of the present invention typically include a separation channel for separating a sample mixture into its various components. For example, a mixture of proteins, as it flows through a separation channel or separation region, is separated into its member proteins. Preferably, the separation channel is a gel filled channel, e.g., a linear polyacrylamide gel filled channel or a polymer solution filled channel, e.g., a polyacrylamide polymer solution, that separates various components based, e.g., on molecular weight, wherein each component is eluted from the separation channel with a different retention time. In this embodiment, the components are then optionally detected and their molecular weights determined by the retention time.

In other embodiments, a separation channel or channel region comprises a separation buffer, e.g., that is flowed into the separation channel region, e.g., from a buffer reservoir. Separation buffers typically comprise, e.g., a polymer matrix, a buffering agent, a detergent, and a dye, e.g., an associative dye or a lipophilic dye.

A binding channel or channel region or an affinity purification zone is typically included in the microfluidic devices and systems in the present invention. The "binding channel," "binding region," "binding channel region," or "affinity purification zone" is typically upstream from a separation channel. The terms "upstream" and "downstream" refer to the relative positioning of the element so described when considered in the context of the direction of flow of the material of interest, e.g., a mixture of components, separated components, or a component of interest, during operation of the system being described. "Upstream" refers to a location in a channel or system of channels that is farther along the channel or plurality of channels in a direction that is opposite the flow of fluid or material flow, relative to a selected site or region. The term "downstream" refers to a location in a channel or microfluidic device that is farther along the channel or plurality of channels in a selected direction of fluid or material flow, relative to a selected site or region. Typically, the phrase upstream refers to the direction of flow toward a sample or buffer reservoir or source connected to a particular channel, while downstream typically refers to the direction toward the waste reservoir connected to a particular channel.

For example, the separation region is farther along in the direction of flow in the channel system than the binding region. Therefore, materials typically flow through the binding region or channel first and then into the separation channel. A component of interest, or a portion thereof, binds to a component-binding moiety in the binding region and remains there as the remaining unbound components of the mixture are separated in the downstream separation region. The component of interest is then typically released and flowed through the separation region in a similar manner.

In some embodiments, the binding channel or region comprises a derivatized channel or channel region. For example, the channel is derivatized with an antibody which binds to a component of interest. The antibody is attached to or associated with the walls of the binding channel or region. Furthermore, myriad different binding moieties can be incorporated into derivatized binding channel areas, depending upon, e.g., the specific component(s) of interest to be bound in the binding region, the surface and/or lining of the channel which comprises the binding channel area, etc. Additionally, levels of derivatization are optionally adjusted to produce the proper density of binding moieties in the binding channel areas for particular assays, etc.

Derivatization of the channel surfaces of binding channel areas optionally includes multiple rounds of additions of, e.g., derivatizing agents, functional groups comprising binding moieties for the component(s) of interest, appropriate buffers, etc. In typical embodiments, one or more rounds of one or more derivatizing agents are contacted to the substrate surface of the microchannel which comprises the binding channel. Such derivatizing agents change/modify the surface of the substrate in the binding region (i.e., they derivatize it) either in preparation for additional steps (such as addition of functional binding moieties) or as a final step (i.e., the derivatization produces the proper binding moieties in the binding region). Alternatively, the round(s) of derivatizing agents are followed by, e.g., one or more rounds of one or more agent which comprises the binding moiety for the component of interest and which binds with and/or interacts with the derivatized surface of the channel comprising the binding region.

Processes of construction of derivatized surfaces capable of incorporation into the devices and methods of the current invention are well known by those in the art. For example, see, e.g., U.S. Pat. No. 5,885,470, "Controlled fluid transport in microfabricated polymeric substrates," issued Mar. 23, 1999 to Parce et al. and U.S. Pat. No. 5,919,523, "Derivatization of solid supports and methods for oligomer synthesis," issued Jul. 6, 1999 to Sundberg et al., both of which are incorporated herein for all purposes.

In other embodiments, the binding channel region comprises one or more particle set, e.g., for binding the component of interest. The particle set in this embodiment typically comprises a plurality of member types comprising one or more of a silica material, a ceramic material, a glass material, a magnetic material, a metallic material, an organic material, or the like. The particle member types typically comprise a component binding moiety to which a component of interest binds, e.g., as it is flowed through the binding region. For example, the component-binding moiety is optionally adsorbed onto one or more member of the particle set. Such particles or beads typically comprise a material such as PVDF, polyamide, nylon, nitrocellulose, or the like. The component of interest typically binds to the component-binding moiety which is adsorbed onto the particles or beads. In other embodiments, the component of interest adsorbs directly onto the particles or beads, where it remains until released. Particles or beads of use in the present invention are typically about 0.1 µm to about 50 µm in diameter and are described in more detail in U.S. Ser. No. 09/510,626 filed Feb. 22, 2000, entitled "Manipulation of Microparticles In Microfluidic Systems," by Mehta et al.

The binding region or affinity purification zone also optionally comprises a stacking region. A stacking region provides a particle retention or capture region for fixing in place a particle set, which is optionally fixed in place or mobile. The particle retention region or stacking region optionally includes a region of increased or decreased microchannel depth or width or other physical barrier (e.g., a groove, mesh, net, matrix, etc.), an electromagnetic field or porous matrix (e.g., sieving matrices), or other means of inhibiting particle movement in, or adjacent to, the stacking region. A particle set stacked in the binding region is typically used to bind a component of interest prior to separation of the mixture of components. For more discussion of particle retention regions, see, U.S. Ser. No. 09/510,626 filed Feb. 22, 2000, entitled "Manipulation of Microparticles In Microfluidic Systems," by Mehta et al.

Other features of the present devices are also optionally included, e.g., upstream or downstream from the binding channel and/or separation channel. For example, a reservoir for a binding buffer or a sample well is optionally upstream from the binding channel or channel region. Reservoirs are locations or wells, e.g., disposed within the device, at which samples, components, reagents, and the like are added into the device for assays to take place. Introduction of these elements into the system is carried out as described below. The reservoirs are typically placed so that a sample or reagent is added into the system upstream from the location at which it is used. For example, diluents are optionally added into a channel comprising separated components upstream from the detection region, e.g., to dilute a detergent concentration prior to detection. In FIG. 3B, a diluent is optionally added into channel 300b from reservoir 380b. The diluent flows from reservoir 380b, through channel 370b and into channel 300b at a region that is upstream from detection region 340b and downstream from separation region 330b. In this manner, the detergent is diluted after the separation is complete yet prior to detection. Alternatively, the diluent is added directly into the detection region. Therefore, diluent channels and reservoirs are optionally included as elements of the present devices. "Diluent channels" are channels that are typically used to transport a diluent or buffer material into a fluidic stream of materials. The diluent is optionally flowed from an internal reservoir or from an external source of materials.

Sipper capillaries are also optionally used to introduce samples into channels of the present devices. A typical sipper capillary is fluidly coupled to a source of a plurality of samples, e.g., a microwell plate, and to a channel disposed within the device. The sipper is used to introduce a sample from the microwell plate into the microfluidic channel system. In the present devices, a sipper capillary would typically be coupled to a channel or channel region upstream from the binding region to introduce samples into the binding regions. In some embodiments, an injection channel is also fluidly coupled to the binding region and the separation region to inject samples from one channel region to the other region.

Another feature optionally present in the devices of the invention is a heating zone. A heating zone is typically a channel or channel region in which components or samples are heated, e.g., prior to separation. For example, a heating zone is typically positioned upstream from a separation region or channel to provide for heating of components prior to separation, e.g., by electrophoresis. Heating zones typically comprise a temperature control element operably coupled to the heating zone, e.g., for heating a mixture of components or a released component of interest, e.g., prior to flowing such components through the separation channel or channel regions. Various channel configurations and/or sizes are optionally used to provide heating zones. Variations in channel thickness and/or voltage applied to a channel are optionally used to selectively heat a particular channel region, e.g., a heating zone. See, e.g., U.S. Pat. No. 6,174,675, issued Jan. 16, 2001, entitled "Electrical Currents for Controlling Fluid Parameters in Microchannels," by Chow et al. For example, joule heating, as provided in U.S. patent application Ser. No. 09/093,832 filed Jun. 8, 1998, entitled "Microfluidic Matrix Localizations Apparatus and Methods," by Mehta and Kopf-Sill, is optionally used. In addition, a separation buffer, e.g., comprising a detergent and/or dye, is optionally added to a mixture of components in the heating region or upstream from the heating region prior to separation.

Detection regions are also included in the present devices. The detection region is optionally a subunit of a channel, or it optionally comprises a distinct channel, that is fluidly coupled to the plurality of channels in the microfluidic device. The detection region is optionally located at the elution point of the separation channel or region or downstream of the elution point, e.g., downstream of a dilution region. For example, a detection region located at the most downstream point or end of the separation channel detects separated components as they are eluted from the separation region or channel.

In some embodiments, a dilution channel intersects a separation channel or a main channel upstream from the detection region or at the detection region to allow dilution of separated components or dilution of the detergent in the separation buffer prior to, or concurrent with, detection.

In other embodiments, the detection region is optionally located at the downstream end of the device just upstream from a waste well. A detection region is optionally located at whatever point in the device that detection of the components is desired. For example, a mixture of components is optionally detected prior to entering the separation channel. Furthermore, multiple detection regions are optionally present in various embodiments of the present invention.

The detection window or region at which a signal is monitored typically includes a transparent cover allowing visual or optical observation and detection of the assay results, e.g., observation of a colorimetric or fluorometric signal or label. Examples of suitable detectors are well known to those of skill in the art and are discussed in more detail below.

One embodiment of the present system is illustrated in FIG. 1. A sample, e.g., a mixture of components, is typically introduced into channel 100, e.g., from a sipper capillary fluidly coupled to channel 100 and a microwell plate comprising a plurality of samples. The sample is typically directed into binding channel region 110. A binding buffer is also optionally added, which binding buffer is optimized to facilitate attachment of a component of interest to a component binding moiety, e.g., a component binding moiety affixed to or adsorbed to a particle set in binding region 110. In binding region 110, the components are mixed with the component-binding moiety, e.g., which is optionally attached to a particle set, which is optionally added into binding region 110 from a particle well or pre-disposed in binding region 110, e.g., in a stacking region located therein. The component binding moiety captures or binds the component of interest or a portion thereof from the mixture of components. The component of interest then remains in binding region 110 as the remaining mixture of components is directed into heating zone 120. In heating zone 120, a detergent, e.g., SDS, is optionally added and the components are heated prior to separation. After the addition of detergent and heat to the mixture of components, the components, e.g., a mixture of proteins, are flowed through separation region 130, in which they are typically separated, e.g., by electrophoresis. A detector is typically positioned to detect the separated components as they elute from separation region 130 into detection region 140. The component of interest in binding region 110 is then typically released from the component-binding moiety, e.g., from a particle set, and flowed through heating zone 120, separation region 130, and detection region 140, e.g., in the same manner as the mixture of components.

In addition, various reservoirs are optionally fluidly connected to channel 100 for storage and/or delivery of materials to detection region 140, separation region 130, heating zone 120, and/or binding region 110, e.g., for delivery of, e.g., washing solutions, blocking solutions, antibodies, diluents, and the like. When the assay and detection are complete, the sample components are optionally directed to a waste well for disposal or retrieval.

Figure 2:
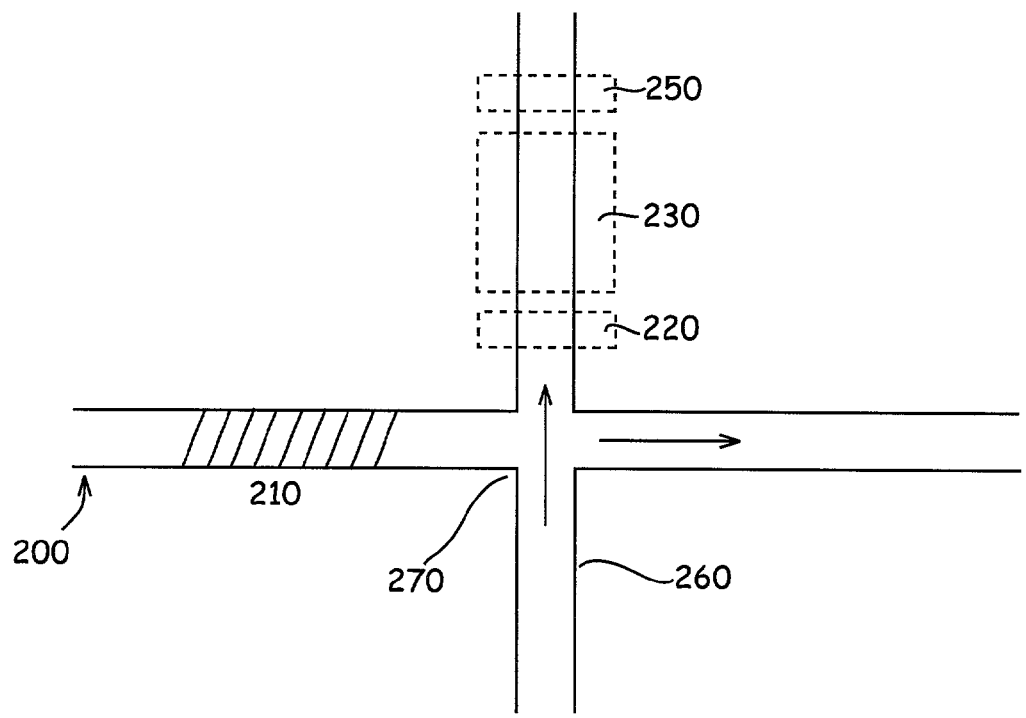
FIG. 2: Schematic of a sample channel structure of the invention, in which the binding region and the separation region comprise separate intersecting channels.

Another embodiment of an affinity purification device is illustrated in FIG. 2. The plurality of channels in FIG. 2 comprises two intersecting channels as described below. A sample is optionally introduced into the device, e.g., through a sample well or sipper capillary fluidly coupled to channel 200. The sample is transported into binding region 210, in which a component of interest binds, e.g., specifically, to a component-binding moiety, e.g., derivatized onto the walls of binding region 210. The component-binding moiety is optionally pre-disposed within binding region 210 or added to binding region 210 from an external or internal source, e.g., a reservoir, whenever a sample is flowed through binding region 210. The bound component of interest remains in binding region 210 as the remaining sample is transported through channel 200 and into intersection 270. At intersection 270, a portion of the sample is cross-injected into channel 260. In other words, the volume of sample material present at the intersection of channels 200 and 260 is flowed into channel 260, e.g., by applying an electrokinetic gradient across channel 260. A separate injection channel is optionally used to perform this cross-injection. Channel 260 comprises heating zone 220, separation region 230, and detection region 250. The cross-injected sample is transported through heating zone 220 and heated prior to separation. In addition, a detergent, e.g., in a separation buffer comprising an associative dye, is also optionally added at this point to the mixture of components, e.g., to the buffer that contains the sample, prior to separation. From heating zone 220, the sample is flowed into separation region 230, where the sample is separated into its individual components, e.g., by electrophoresis.

Side channels and reservoirs are also optionally included in the device to introduce buffers, washing solutions, detergents, diluents, and the like, into channel 200 and/or channel 260. When the assay of interest is complete and the component(s) of interest and separated components have been detected, the components are then optionally directed into a waste well, e.g., downstream from detection region 250, for disposal or retrieval.

Figure 3A:
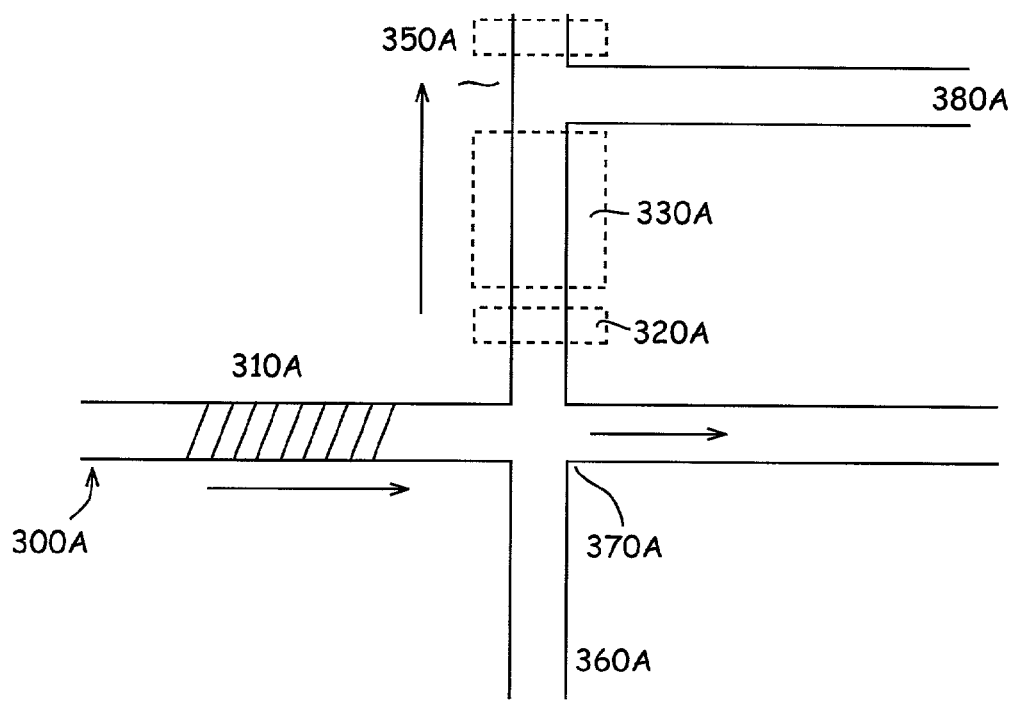
FIG. 3: Panels A and B illustrate the device of FIGS. 1 and 2 when dilution channels are included.
Figure 3B:
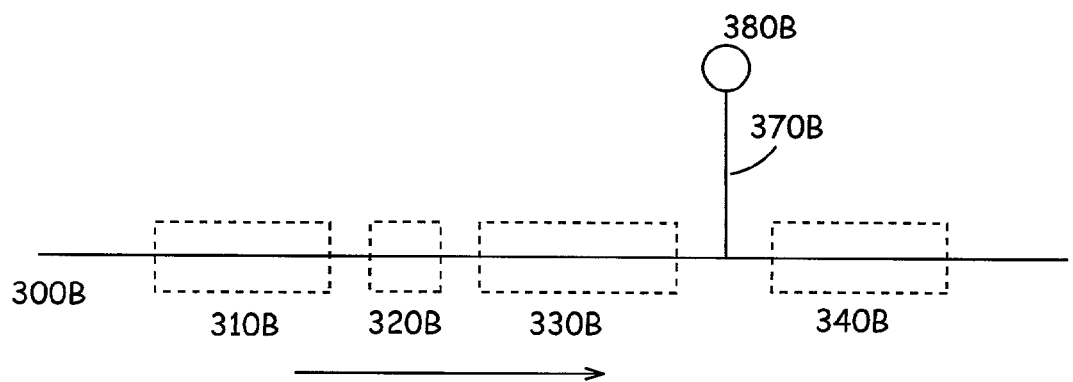

In other embodiments illustrated in FIGS. 3A and 3B, dilution channels and reservoirs are included, e.g., for diluting detergents in the separation buffer before detecting the separated components or a released component of interest. FIG. 3B is typically used as described above for the device of FIG. 1. Dilution channel 370b is used to add a diluent, buffer, or other fluidic material from reservoir 380b into channel 300b downstream from separation region 330b. Typically the diluent is added into channel 300b upstream from detection region 340b or directly into detection region 340b. Therefore diluent channel 370b optionally intersects channel 300b in detection region 340b or upstream from detection region 340b. The device in FIG. 3A is typically used as described above for FIG. 2. Diluent channel 380a is shown, through which a diluent material, e.g., a buffer or other fluidic material, is flowed into channel 360a downstream from separation region 330a and upstream from, or into, detection region 350a.

Figure 4:
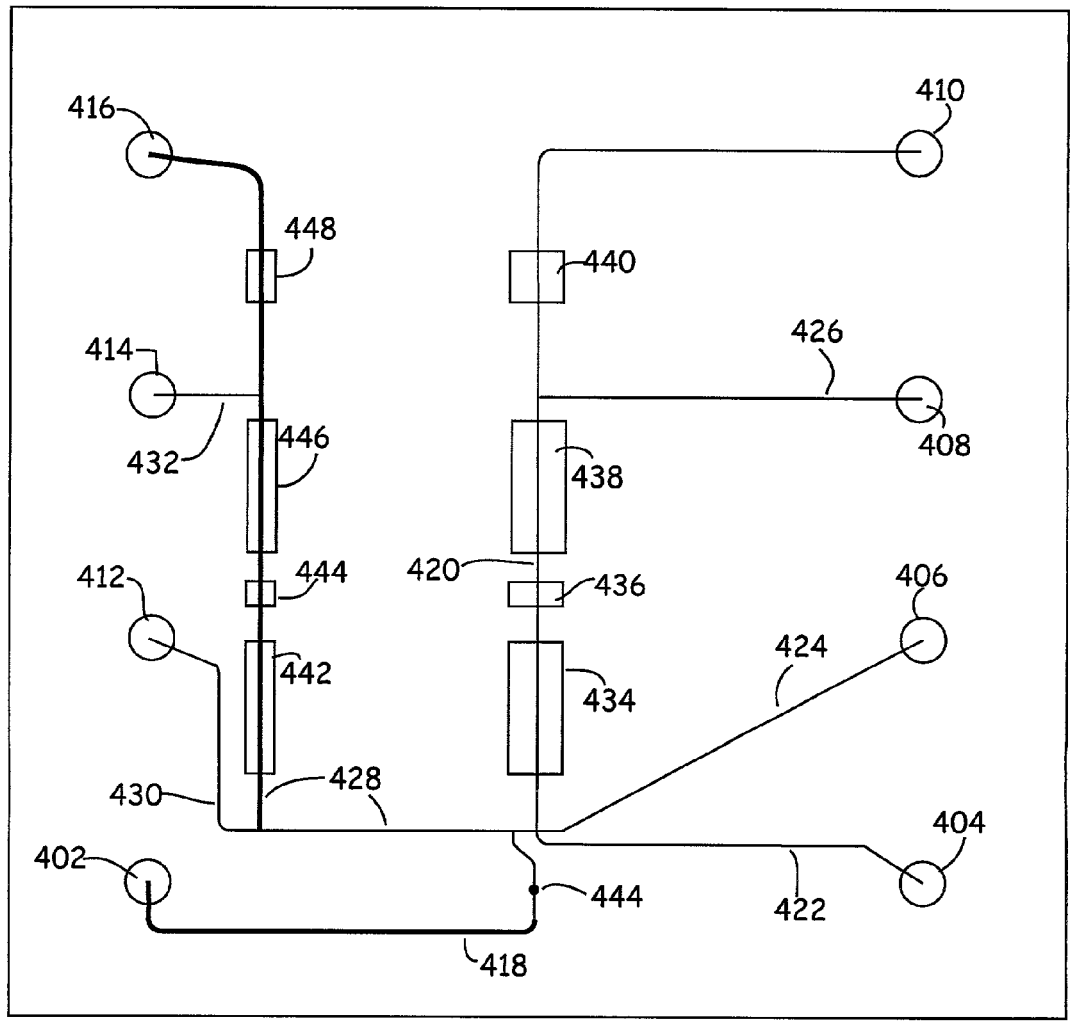
FIG. 4: Schematic of a sample microfluidic chip of the invention, in which binding regions and separation regions comprise single channels.

FIG. 4 illustrates one possible microfluidic chip incorporating the devices of the current invention. As shown in FIG. 4, microfluidic chip 400, incorporates reservoir, 402, which comprises a sample to be assayed, e.g., a mixture of components, cell lysate, etc. Such sample is flowed from reservoir 402 through channel 418 (typically via pressure as explained herein). Alternatively, samples to be assayed are stored separated from the microfluidic chip (e.g., in a microwell plate) and are accessed through, e.g., a micropipettor or other similar element. Such samples are flowed into chip 400 through junction 444 (i.e., where, e.g., a micropipettor attaches to the channel network in chip 400). Where samples are flowed into chip 400 from an outside storage site, the fluidic material flowed from reservoir 402 can comprise, e.g., a dilution buffer, etc. Chip 400, as illustrated, comprises two sets of binding regions (434 and 442), two sets of heating regions (436 and 444), two sets of separation regions (438 and 446), and two sets of detection regions (440 and 448).

The arrangement of regions and channels in chip 400 allows for, e.g., two different components of interest to be analyzed, i.e., one through channel 420 via regions 434, 436, 438, and 440 and the other through channel 428 via regions 442, 444, 446, and 448. It should be appreciated that chip 400 comprises only one of myriad possible channel/region arrangements utilizing the methods and devices of the current invention. Both more complexity (i.e., more channels, more binding regions, etc.) and more simplicity (i.e., only one main channel, only one main binding region, etc.) are optional embodiments of the current invention.

The mixture of sample, whether from reservoir 402 or from an outside storage region through junction 444, is alternatively flowed through channel 420. Various buffers, as described herein, or other reagents, etc. are optionally flowed into channel 420 from reservoirs 406 and 404, including, e.g., putative receptors of components in the sample, inhibitors of components in the sample, detergents, etc. The mixture (i.e., sample, components, etc.) is then flowed through binding region 434, wherein the one or more component of interest is bound (i.e., as described herein). The unbound fraction of the sample continues to flow through channel 420 to heating region 436 and thence to separation region 438 where the components of the sample are electrophoretically separated. Also, as shown in FIG. 4, a diluent is optionally flowed from reservoir 408 through channel 426 and into channel 420. As described herein, such diluent, e.g., decreases the concentration of detergent in the separated sample (i.e., the sample that has been electrophoretically separated into its constituent parts) in order to prevent or ameliorate the formation of detergent micelles which can trap staining dyes and lead to problematical background readings. The separated components are then flowed through detection region 440 and the electrophoretically separated components are quantitated and/or assessed qualitatively.

The bound component(s) of interest (i.e., bound in binding region 434) is released, e.g., after the separated components are flowed past. The released component of interest then flows through the same regions in channel 420 as did the separated components (i.e., 434, 436, etc.). Similar dilution of detergent (i.e., via diluent from reservoir 408) is also optionally utilized to prevent/ameliorate micelle formation when the release component of interest is flowed through detection region 440. The released component of interest is then detected in detection region 440 and the quantitation and/or qualitative assessment is then compared with the measurements of the separated components as described herein.

Alternatively and/or additionally, the sample mixture is flowed through channel 428. The process of binding, separating, detecting, releasing, etc. as done in channel 420 and its regions, is repeated in channel 428 and its regions with only minor variations (e.g., only one reservoir communicates with channel 428 before the binding region).

Again, as will be appreciated from FIG. 4, the devices and methods of the current invention allow for incorporation of western blot type assays in numerous configurations of microfluidic chips.

A variety of microscale systems are optionally adapted to the present invention by incorporating separations gels, particle sets, antibodies, detergents, dyes, diluents, dilution buffers, and the like into the devices as described above. Microfluidic devices which can be adapted to the present invention by the addition of assay components, e.g., western assay components, are described in various PCT applications and issued U.S. patents by the inventors and their coworkers, including U.S. Pat. No. 5,699,157 (J. Wallace Parce) issued Dec. 16, 1997, U.S. Pat. No. 5,779,868 (J. Wallace Parce et al.) issued Jul. 14, 1998, U.S. Pat. No. 5,800,690 (Calvin Y. H. Chow et al.) issued Sep. 1, 1998, U.S. Pat. No. 5,842,787 (Anne R. Kopf-Sill et al.) issued Dec. 1, 1998, U.S. Pat. No. 5,852,495 (J. Wallace Parce) issued Dec. 22, 1998, U.S. Pat. No. 5,869,004 (J. Wallace Parce et al.) issued Feb. 9, 1999, U.S. Pat. No. 5,876,675 (Colin B. Kennedy) issued Mar. 2, 1999, U.S. Pat. No. 5,880,071 (J. Wallace Parce et al.) issued Mar. 9, 1999, U.S. Pat. No. 5,882,465 (Richard J. McReynolds) issued Mar. 16, 1999, U.S. Pat. No. 5,885,470 (J. Wallace Parce et al.) issued Mar. 23, 1999, U.S. Pat. No. 5,942,443 (J. Wallace Parce et al.) issued Aug. 24, 1999, U.S. Pat. No. 5,948,227 (Robert S. Dubrow) issued Sep. 7, 1999, U.S. Pat. No. 5,955,028 (Calvin Y. H. Chow) issued Sep. 21, 1999, U.S. Pat. No. 5,957,579 (Anne R. Kopf-Sill et al.) issued Sep. 28, 1999, U.S. Pat. No. 5,958,203 (J. Wallace Parce et al.) issued Sep. 28, 1999, U.S. Pat. No. 5,958,694 (Theo T. Nikiforov) issued Sep. 28, 1999, U.S. Pat. No. 5,959,291 (Morten J. Jensen) issued Sep. 28, 1999, U.S. Pat. No. 5,964,995 (Theo T. Nikiforov et al.) issued Oct. 12, 1999, U.S. Pat. No. 5,965,001 (Calvin Y. H. Chow et al.) issued Oct. 12, 1999, U.S. Pat. No. 5,965,410 (Calvin Y. H. Chow et al.) issued Oct. 12, 1999, U.S. Pat. No. 5,972,187 (J. Wallace Parce et al.) issued Oct. 26, 1999, U.S. Pat. No. 5,976,336 (Robert S. Dubrow et al.) issued Nov. 2, 1999, U.S. Pat. No. 5,989,402 (Calvin Y. H. Chow et al.) issued Nov. 23, 1999, U.S. Pat. No. 6,001,231 (Anne R. Kopf-Sill) issued Dec. 14, 1999, U.S. Pat. No. 6,011,252 (Morten J. Jensen) issued Jan. 4, 2000, U.S. Pat. No. 6,012,902 (J. Wallace Parce) issued Jan. 11, 2000, U.S. Pat. No. 6,042,709 (J. Wallace Parce et al.) issued Mar. 28, 2000, U.S. Pat. No. 6,042,710 (Robert S. Dubrow) issued Mar. 28, 2000, U.S. Pat. No. 6,046,056 (J. Wallace Parce et al.) issued Apr. 4, 2000, U.S. Pat. No. 6,048,498 (Colin B. Kennedy) issued Apr. 11, 2000, U.S. Pat. No. 6,068,752 (Robert S. Dubrow et al.) issued May 30, 2000, U.S. Pat. No. 6,071,478 (Calvin Y. H. Chow) issued Jun. 6, 2000, U.S. Pat. No. 6,074,725 (Colin B. Kennedy) issued Jun. 13, 2000, U.S. Pat. No. 6,080,295 (J. Wallace Parce et al.) issued Jun. 27, 2000, U.S. Pat. No. 6,086,740 (Colin B. Kennedy) issued Jul. 11, 2000, U.S. Pat. No. 6,086,825 (Steven A. Sundberg et al.) issued Jul. 11, 2000, U.S. Pat. No. 6,090,251 (Steven A. Sundberg et al.) issued Jul. 18, 2000, U.S. Pat. No. 6,100,541 (Robert Nagle et al.) issued Aug. 8, 2000, U.S. Pat. No. 6,107,044 (Theo T. Nikiforov) issued Aug. 22, 2000, U.S. Pat. No. 6,123,798 (Khushroo Gandhi et al.) issued Sep. 26, 2000, U.S. Pat. No. 6,129,826 (Theo T. Nikiforov et al.) issued Oct. 10, 2000, U.S. Pat. No. 6,132,685 (Joseph E. Kersco et al.) issued Oct. 17, 2000, U.S. Pat. No. 6,148,508 (Jeffrey A. Wolk) issued Nov. 21, 2000, U.S. Pat. No. 6,149,787 (Andrea W. Chow et al.) issued Nov. 21, 2000, U.S. Pat. No. 6,149,870 (J. Wallace Parce et al.) issued Nov. 21, 2000, U.S. Pat. No. 6,150,119 (Anne R. Kopf-Sill et al.) issued Nov. 21, 2000, U.S. Pat. No. 6,150,180 (J. Wallace Parce et al.) issued Nov. 21, 2000, U.S. Pat. No. 6,153,073

(Robert S. Dubrow et al.) issued Nov. 28, 2000, U.S. Pat. No. 6,156,181 (J. Wallace Parce et al.) issued Dec. 5, 2000, U.S. Pat. No. 6,167,910 (Calvin Y. H. Chow) issued Jan. 2, 2001, U.S. Pat. No. 6,171,067 (J. Wallace Parce) issued Jan. 9, 2001, U.S. Pat. No. 6,171,850 (Robert Nagle et al.) issued Jan. 9, 2001, U.S. Pat. No. 6,172,353 (Morten J. Jensen) issued Jan. 9, 2001, U.S. Pat. No. 6,174,675 (Calvin Y. H. Chow et al.) issued Jan. 16, 2001, U.S. Pat. No. 6,182,733 (Richard J. McReynolds) issued Feb. 6, 2001, U.S. Pat. No. 6,186,660 (Anne R. Kopf-Sill et al.) issued Feb. 13, 2001, U.S. Pat. No. 6,221,226 (Anne R. Kopf-Sill) issued Apr. 24, 2001, and U.S. Pat. No. 6,233,048 (J. Wallace Parce) issued May 15, 2001.

Systems adapted for use with the devices and components comprising the devices and methods of the present invention are also described in, e.g., various published PCT applications, such as, WO 98/00231, WO 98/00705, WO 98/00707, WO 98/02728, WO 98/05424, WO 98/22811, WO 98/45481, WO 98/45929, WO 98/46438, and WO 98/49548, WO 98/55852, WO 98/56505, WO 98/56956, WO 99/00649, WO 99/10735, WO 99/12016, WO 99/16162, WO 99/19056, WO 99/19516, WO 99/29497, WO 99/31495, WO 99/34205, WO 99/43432, WO 99/44217, WO 99/56954, WO 99/64836, WO 99/64840, WO 99/64848, WO 99/67639, WO 00/07026, WO 00/09753, WO 00/10015, WO 00/21666, WO 00/22424, WO 00/26657, WO 00/42212, WO 00/43766, WO 00/45172, WO 00/46594, WO 00/50172, WO 00/50642, WO 00/58719, WO 00/60108, WO 00/70080, WO 00/70353, WO 00/72016, WO 00/73799, WO 00/78454, WO 01/02850, WO 01/14865, WO 01/17797, and WO 01/27253.

For example, pioneering technology providing cell based microscale assays, e.g., in planar and sipper format, are set forth in U.S. Pat. No. 5,942,443, by Parce et al. "High Throughput Screening Assay Systems in Microscale Fluidic Devices" and, e.g., in 60/128,643 filed Apr. 4, 1999 and Ser. No. 09/510,626 filed Feb. 22, 2000, both entitled "Manipulation of Microparticles In Microfluidic Systems," by Mehta et al. Complete integrated systems with fluid handling, signal detection, sample storage and sample accessing are available. For example, U.S. Pat. No. 5,942,443 provides pioneering technology for the integration of microfluidics and sample selection and manipulation.

General Fluid Flow Techniques in Microfluidic Devices

In general, enzymes, proteins, antibodies, cells, modulators and other components are flowed in a microscale system by electrokinetic (including either electroosmotic or electrophoretic) techniques, or using pressure-based flow mechanisms, or combinations thereof. In the present system, the control systems used to direct fluid flow typically include a combination of electrokinetic transport and pressure-based transport. For example, pressure is optionally used to flow samples through a binding channel and electrokinetic transport is used to inject samples into and flow samples through a separation channel in the present devices.

Electrokinetic material transport systems, e.g., electrokinetic controllers or electrokinetic fluid control elements, are used in microfluidic devices, e.g., planar and/or sipper devices, to provide movement of samples, mixtures of components, components of interest, component-binding moieties, proteins, antibodies, enzymes, substrates, particle sets, and the like, through microfluidic channels, e.g., using an electrokinetic gradient set up across a channel or channel junction. "Electrokinetic material transport systems," as used herein, include systems that transport and direct materials within a microchannel and/or chamber containing structure, through the application of electrical fields to the materials, thereby causing material movement through and among the channel and/or chambers, i.e., cations will move toward a negative electrode, while anions will move toward a positive electrode. For example, movement of fluids toward or away from a cathode or anode can cause movement of proteins, nucleic acids, enzymes, cells, modulators, etc. suspended within the fluid. Similarly, the components, e.g., proteins, antibodies, carbohydrates, etc. can be charged, in which case they will move toward an oppositely charged electrode (indeed, in this case, it is possible to achieve fluid flow in one direction while achieving particle flow in the opposite direction). In this embodiment, the fluid can be immobile or flowing and can comprise a matrix as in electrophoresis. For example, a mixture of proteins is separated based on mass/charge ratio in a channel comprising a separation matrix, such as polyacrylamide.

Typically, the electrokinetic material transport and direction systems of the invention rely upon the electrophoretic mobility of charged species within the electric field applied to the structure. Such systems are more particularly referred to as electrophoretic material transport systems. For example, in the present system, separation of a mixture of components into its individual components optionally occurs by electrophoretic separation. For electrophoretic applications, the walls of interior channels of the electrokinetic transport system are optionally charged or uncharged. Typical electrokinetic transport systems are made of glass, charged polymers, and uncharged polymers. The interior channels are optionally coated with a material that alters the surface charge of the channel.

A variety of electrokinetic controllers and control systems which are optionally used in the present invention are described, e.g., in Ramsey WO 96/04547, Parce et al. WO 98/46438 and Dubrow et al., WO 98/49548, as well as a variety of other references noted herein.

Use of electrokinetic transport to control material movement in interconnected channel structures was described, e.g., in WO 96/04547 and U.S. Pat. No. 5,858,195 by Ramsey. An exemplary controller is described in U.S. Pat. No. 5,800,690. Modulating voltages are concomitantly applied to the various reservoirs to affect a desired fluid flow characteristic, e.g., continuous or discontinuous (e.g., a regularly pulsed field causing the sample to oscillate direction of travel) flow of labeled components in one or more channels toward a waste reservoir. Particularly, modulation of voltages applied at various reservoirs, e.g., between two reservoirs located at either end of channel 260 in FIG. 2, injects the volume of fluid at junction 270 into channel 260. In this instance, channel 200 serves as an injection channel for injecting samples into the separation channel, e.g., channel 260.

Other methods of transport are also available for situations in which electrokinetic methods are not desirable. For example, sample introduction and reaction are optionally carried out in a pressure-based system and high throughput systems typically use pressure induced sample introduction. In addition, cells are desirably flowed using pressure-based flow mechanisms.

Pressure based flow is also desirable in systems in which electrokinetic transport is also used. For example, pressure based flow is optionally used for introducing and reacting reagents in a system in which the products are electrophoretically separated. In the present system, a combination of pressure based flow and electrokinetic based flow is typically used. For example, a pressure based control system is typically used to introduce samples, e.g., mixtures of components, into a binding channel in which a component of interest is bound to a component-binding moiety, and electrokinetic based flow is typically used to separate the mixture of components into its individual components.

Pressure is optionally applied to microscale elements to achieve fluid movement using any of a variety of techniques. Fluid flow (and flow of materials suspended or solubilized within the fluid, including cells or other particles) is optionally regulated by pressure based mechanisms or pressure based fluid control elements, e.g., as part of a fluid direction or control system, such as those based upon fluid displacement, e.g., using a piston, pressure diaphragm, vacuum pump, probe, or the like to displace liquid and raise or lower the pressure at a site in the microfluidic system. The pressure is optionally pneumatic, e.g., a pressurized gas, or uses hydraulic forces, e.g., pressurized liquid, or alternatively, uses a positive displacement mechanism, e.g., a plunger fitted into a material reservoir, for forcing material through a channel or other conduit, or is a combination of such forces.

In some embodiments, a vacuum source is applied to a reservoir or well at one end of a channel to draw the suspension through the channel. For example, a vacuum source is optionally placed at a reservoir located downstream from the detection region in the present devices for drawing fluid into a channel, e.g., a vacuum source at a reservoir positioned at the downstream end of channel 100 in FIG. 1 applies a pressure to channel 100, thus drawing fluid, e.g., from a reservoir, sipper capillary, or the like, through channel 100, e.g., through binding region 110 and heating zone 120.

Pressure or vacuum sources are optionally supplied external to the device or system, e.g., external vacuum or pressure pumps sealably fitted to the inlet or outlet of the channel, or they are internal to the device, e.g., microfabricated pumps integrated into the device and operably linked to the channel. Examples of microfabricated pumps have been widely described in the art. See, e.g., published International Application No. WO 97/02357.

Another alternative to electrokinetic transport is an electroosmotic pump which uses electroosmotic forces to generate pressure based flow. See, e.g., published International Application No. WO 99/16162 by Parce, entitled "Micropump." An electroosmotic pump typically comprises two channels. The pump utilizes electroosmotic pumping of fluid in one channel or region to generate pressure based fluid flow in a connected channel, where the connected channel has substantially no electroosmotic flow generated. For example, an electrokinetic controller applies a voltage gradient to one channel to produce electroosmotically induced pressure within that channel. That pressure is transmitted to a second channel whereupon pressure based flow is achieved. In the present invention, an electroosmotic pump is optionally used to produce pressure-based flow, e.g., in a binding channel. The channel surfaces of the pumping channel typically have charged functional groups associated therewith to produce sufficient electroosmotic flow to generate pressure in the channels in which no electroosmotic flow takes place. See, WO 99/16162 for appropriate types of functional groups.

Hydrostatic, wicking, and capillary forces are also optionally used to provide pressure for fluid flow of materials such as protein mixtures, proteins of interest, dyes, detergents, component-binding-moieties, and the like. See, e.g., "METHOD AND APPARATUS FOR CONTINUOUS LIQUID FLOW IN MICROSCALE CHANNELS USING PRESSURE INJECTION, WICKING AND ELECTROKINETIC INJECTION," by Alajoki et al., U.S. Ser. No. 09/245,627, filed Feb. 5, 1999. In these methods, an absorbent material or branched capillary structure is placed in fluidic contact with a region where pressure is applied, thereby causing fluid to move towards the absorbent material or branched capillary structure. The capillary forces are optionally used in conjunction with the electrokinetic or pressure-based flow in the present invention. The capillary action pulls material through a channel. For example a wick is optionally added to a main channel to aid fluid flow by drawing liquid, e.g., a mixture of components, such as proteins, through the channel.

Mechanisms for reducing adsorption of materials during fluid-based flow are described in "PREVENTION OF SURFACE ADSORPTION IN MICROCHANNELS BY APPLICATION OF ELECTRIC CURRENT DURING PRESSURE-INDUCED FLOW" U.S. Ser. No. 09/310,027, filed May 11, 1999 by Parce et al. In brief, adsorpotion of cells, components, proteins, antibodies, and other materials to channel walls or other microscale components during pressure-based flow is optionally reduced by applying an electric field such as an alternating current to the material during flow.

Mechanisms for focusing cells, enzymes, and other components into the center of microscale flow paths, which are useful in increasing assay throughput by regularizing flow velocity, e.g., in pressure based flow, are described in "FOCUSING OF MICROPARTICLES IN MICROFLUIDIC SYSTEMS" by H. Garrett Wada et al., U.S. Ser. No. 09/569,747, filed May 11, 1999. In brief, sample materials are focused into the center of a channel by forcing fluid flow from opposing side channels into a main channel comprising the sample materials, or by other fluid manipulations.

In an alternative embodiment, microfluidic systems are incorporated into centrifuge rotor devices, which are spun in a centrifuge. Fluids and particles travel through the device due to gravitational and centripetal/centrifugal pressure forces. For example, samples are optionally transported through a main channel of a planar device using centrifugal force.

In addition to transport through the microfluidic system, the invention also provides for introduction of sample or reagents, e.g., sample mixtures, proteins, antibodies, dyes, buffers, and the like, into the microfluidic system.

Reservoirs or wells are provided in the present devices as sources of buffers, component-binding moieties, washing solutions, detergents, and the like. Such wells include, e.g., diluent well 380b in FIG. 3b. Additional reservoirs are optionally present, e.g., for the sample or mixture of components to be tested for the component of interest and for a particle set comprising a component-binding moiety to be used in binding a mixture of components.

Sources of samples, mixtures of components, and reagents, e.g., washing solutions, blocking solutions, dyes, detergents, diluents, and the like, are fluidly coupled to the microchannels noted herein in any of a variety of ways. In particular, those systems comprising sources of materials set forth in Knapp et al. "Closed Loop Biochemical Analyzers" (WO 98/45481; PCT/US98/06723) and Parce et al. "High Throughput Screening Assay Systems in Microscale Fluidic Devices" WO 98/00231 and, e.g., in 60/128,643 filed Apr. 4, 1999, entitled "Manipulation of Microparticles In Microfluidic Systems," by Mehta et al. are applicable.

In these systems, a "pipettor channel" or "sipper capillary" (a channel in which components can be moved from a source, such as a microwell plate, to a microscale element such as a second channel or reservoir) is temporarily or permanently coupled to a source of material. The source can be internal or external to a microfluidic device comprising the pipettor channel. Example sources include microwell plates, membranes or other solid substrates comprising lyophilized components, wells or reservoirs in the body of the microscale device itself and others. For example, a sipper capillary is optionally used to sample a plurality of mixtures from a microwell plate and introduce them, e.g., serially, into the devices described above.

For example, the source of a sample, component, mixture of components, or buffer can be a microwell plate external to the body structure, having, e.g., at least one well with the selected sample or mixture of components. Alternatively, the source of a sample, component, mixture of components, buffer, etc. can comprise a well disposed on the surface of the body structure comprising the selected component; a reservoir disposed within the body structure comprising the selected component, mixture of components, or reagent; a container external to the body structure comprising at least one compartment comprising the selected particle type, component, or reagent; or a solid phase structure comprising the selected component or reagent in lyophilized or otherwise dried form.

A loading channel region is optionally fluidly coupled to a pipettor channel with a port external to the body structure. The loading channel can be coupled to an electropipettor channel with a port external to the body structure, a pressure-based pipettor channel with a port external to the body structure, a pipettor channel with a port internal to the body structure, an internal channel within the body structure fluidly coupled to a well on the surface of the body structure, an internal channel within the body structure fluidly coupled to a well within the body structure, or the like.

The integrated microfluidic system of the invention optionally includes a very wide variety of storage elements for storing reagents to be assessed. These include well plates, matrices, membranes and the like. The reagents are stored in liquids (e.g., in a well on a microtiter plate), or in lyophilized form (e.g., dried on a membrane or in a porous matrix), and can be transported to an array component, region, or channel of the microfluidic device using conventional robotics, or using an electropipettor or pressure pipettor channel fluidly coupled to a region or channel of the microfluidic system.

Another type of reagent optionally included in or introduced into the above devices is a particle set, made from particle member types. The particle set is used for binding or adsorbing components, e.g., a component of interest such as a specific protein, in a binding region. The particle set is optionally used to remove the component of interest from a fluid stream comprising a mixture of components, e.g., by binding the component of interest to a component binding moiety attached to the particle. The component of interest is then typically released from the particle set and detected.

The particle member types typically comprise one of the following: a polymeric material, a silica material, a ceramic material, a glass material, a magnetic material, a metallic material, an organic material, or the like. For example, the particles optionally comprise polymer or ceramic beads. Preferably, the particle member types or beads comprise PVDF, nitrocellulose, or polyamide, e.g., nylon.

The particle member types are optionally stored in a well or reservoir, such as a particle well fluidly coupled to a binding region, and released into the device or system as needed or contained within the binding region or channel in which they will be used. For example, particles are optionally released from a particle well into binding region 110 as shown in FIG. 1, e.g., and stacked using a particle retention area. The particles may be stored and introduced as described above. Additional information on storage, placement and usage of particle sets in microfluidic devices is found, e.g., in U.S. Ser. No. 09/510,626 filed Feb. 22, 2000, entitled "Manipulation of Microparticles In Microfluidic Systems," by Mehta et al.

In general, a mixture of compounds is typically introduced into an assay system as described above, e.g., into a binding region to specifically bind a component of interest. The mixture is then separated into its various components, e.g., proteins. The separated components are detected and then the bound component of interest is released from the binding region and detected. The component of interest is then optionally identified using a superposition of the results of the two detections.

The above devices, systems, features, and components are used as described below, e.g., to separate a mixture of components, to perform affinity purification assays, to perform western assays, to separate and/or sequence nucleic acids, to screen a drug library, to detect a component of interest in a mixture of components, to perform fluorescence polarization assays, mobility shift assays, and the like.

II. Affinity Binding

A mixture of components is introduced into a microfluidic system as described above, e.g., through a sample reservoir, sipper capillary, or the like. The sample is then flowed through an affinity purification zone or binding channel region. Such channel regions are described above. A component-binding moiety is typically positioned within the binding region, e.g., adsorbed onto a particle set or derivatized to the channel walls, to contact the mixture of components. As the mixture of components is flowed, e.g., using pressure based flow, through the binding region, the component-binding moiety specifically binds to a component of interest within the mixture, if one is present. This removes the component of interest, or a portion thereof, from the mixture of components. The mixture of components is then optionally separated and detected separately from the component of interest, allowing identification of the later detected component of interest.

A "mixture of components," as used herein, refers to a combination, known or unknown, of biological components, e.g., proteins, carbohydrates, or nucleic acids. The components can be in a complex mixture, such as blood, serum, cell extracts, or in a purified solution, such as a buffered solution of proteins.

The mixture of components is optionally labeled with a detectable label that allows detection of the components, including the component of interest. The label is optionally a fluorescent label, a chemiluminescent label, an enzyme label, or a colorimetric label. In other embodiments, an associative dye is used to detect components. Such dyes associate with or attach to specific components, e.g., proteins, and are used for detection as described below. These dyes are optionally added with the mixture of compounds to the binding affinity region or they can be added later, e.g., prior to separation or detection.

A "label" is any composition detectable by spectroscopic, photochemical, biochemical, immunochemical, electrical, optical or chemical means. Useful labels in the present invention include fluorescent dyes (e.g., fluorescein isothiocyanate, Texas red, rhodamine, and the like), radiolabels (e.g., 3H, 125I, 35S, 14C, 32P, 33P, etc.), enzymes (e.g., horseradish peroxidase, alkaline phosphatase etc.), and colorimetric labels such as gold colored glass or plastic (e.g., polystyrene, polypropylene, latex, etc.) beads.

The label is coupled directly or indirectly to a component of the assay according to methods well known in the art. As indicated above, a wide variety of labels are used, with the choice of label depending on the sensitivity required, ease of conjugation with the component of interest or the component-binding moiety, stability requirements, available instrumentation and disposal provisions. Non-radioactive labels are often attached by indirect means. Generally, a ligand molecule (e.g., biotin) is covalently bound to the component to be labeled. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands are optionally used. Where a ligand has a natural anti-ligand, for example, biotin, thyroxine, or cortisol, it is used in conjunction with the labeled naturally occurring anti-ligand. Alternatively, any haptogenic or antigenic compound is used in combination with an antibody (see, e.g., Coligan (1991) *Current Protocols in Immunology*, Wiley/Greene, NY; and Harlow and Lane (1989) *Antibodies: A Laboratory Manual*, Cold Spring Harbor Press, NY for a general discussion of how to make and use antibodies). The components of the invention are also optionally conjugated directly to signal-generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include, e.g., luciferin and 2,3,-dihydrophthalalzinediones, e.g., luminol, and the like.

For example, an antibody is preferably labeled with an enzyme or other label. The enzyme label is optionally a hydrolase such as alkaline phosphatase that is used with dioxetane substrates to generate chemiluminescence that is screened and which can be scanned by the same detector used for the detection of electrophoretic mobility. Alternatively, a linear or 2-dimensional array CCD detector is used to measure the chemiluminescence. There are also fluorescent substrates for alkaline phosphatase that precipitate in situ when hydrolyzed and thereby deposit fluorescent dye where the enzyme label is present. The fluorescence is optionally detected by a fluorescence detector that is scanned along a detection channel region.

In one embodiment, a component-binding moiety of the present invention is optionally a "protein-binding moiety" specific to a protein of interest. The protein-binding moiety is any molecule, e.g., a protein, a nucleic acid, an antibody, an enzyme, or the like, that specifically binds to a protein of interest in the present invention. The phrase "specifically binds" to a protein or component refers to a binding reaction that is determinative of the presence of the protein in a heterogeneous population of proteins, components, and other biologics. Thus when a protein-binding moiety specific to a protein of interest binds to that protein (or when a component-binding moiety specific to a component of interest binds to the component of interest) it binds to that particular protein or component preferentially out of a complex mixture. For example, it binds at least two times the background, more typically 10 to 100 times background, and does not substantially bind in significant amounts to other proteins or components in the sample. Specific binding to a polyclonal antibody may require an antibody that is selected for its specificity for a particular protein or component as discussed below.

In one typical embodiment, the "component-binding moiety" is a "protein-binding moiety," such as an antibody, receptor, or ligand. An "antibody" is a multifunctional glycoprotein produced in nature by an immune system. Antibodies function in the immune system to prevent infection by microorganisms. They perform this function by recognizing and binding to particular molecular configurations on invading microorganisms, each antibody being able to bind only one or a small number of related molecular configurations or antigens. Typically, an antibody comprises a framework from an immunoglobulin gene or fragment that specifically binds and recognizes the antigen. The recognized immunoglobulin genes include the kappa, lambda, alpha, gamma, delta, epsilon, and mu constant region genes as well as the various immunoglobulin variable genes. Light chains are classified as either kappa or lambda. Heavy chains are classified as gamma, mu, alpha, delta, or epsilon, which define the immunoglobin classes, IgG, IgM, IgA, IgD, and IgE.

An exemplary immunglobulin or antibody structural unit comprises a tetramer. Each tetramer is composed of two identical pairs of polypeptide chains, each pair having one light and one heavy chain. The N-terminus of each chain defines a variable region of about 100-110 or more amino acids primarily responsible for antigen recognition.

Antibodies exist as intact immunoglobulins or as a number of well-characterized fragments produced by digestion with various peptidases. While various antibody fragments are defined in terms of the digestion of an intact antibody, one of skill will recognize that such fragments may be synthesized de novo either chemically or by using recombinant DNA technology.

For preparation of monoclonal or polyclonal antibodies, any technique known in the art is optionally used. (see, e.g., Paul (ed.) (1993) *Fundamental Immunology, Third Edition* Raven Press, Ltd., New York Coligan (1991) *Current Protocols in Immunology* Wiley/Greene, NY; Harlow and Lane (1989) *Antibodies: A Laboratory Manual* Cold Spring Harbor Press, NY; Stites et al. (eds.) *Basic and Clinical Immunology* (4th ed.) Lange Medical Publications, Los Altos, Calif., and references cited therein; Goding (1986) *Monoclonal Antibodies: Principles and Practice* (2d ed.) Academic Press, New York, N.Y.; and Kohler and Milstein (1975) *Nature* 256:495-497. Other suitable techniques for antibody preparation include selection of libraries of recombinant antibodies in phage or similar vectors. See, Huse et al. (1989) *Science* 246:1275-1281; and Ward et al. (1989) *Nature* 341: 544-546. Specific monoclonal and polyclonal antibodies and antisera will usually bind with a KD of at least about 0.1 µM, preferably at least about 0.01 µM or better, and most typically and preferably, 0.001 µM or better.

In other embodiments, the component-binding moiety comprises biotin, avidin, a lectin, small organic molecule or the like. For example, when the component of interest is a carbohydrate, the component-binding moiety is preferably a lectin, e.g., a glycoprotein that binds oligosaccharides or carbohydrates typically through precise and/or stereospecific interactions. Another specifically binding system of interest in the present invention is the avidin-biotin system. Biotin is optionally linked to proteins or nucleic acids and used as a label. Detection of a biotinylated protein or nucleic acid occurs due to the enzymatic or chemiluminescent reaction of biotin with a detector complex comprising streptavidin or avidin, which binds tightly to the biotin. The "component-binding moiety" is a molecule or substance that binds to the component of interest.

In the binding region or affinity purification zone, the mixture of components is contacted with a component-binding moiety that is specific to a component of interest. In one embodiment, the mixture of components is introduced into the binding channel region, e.g., in a binding buffer. Binding buffers are optionally provided to aid the binding of the component of interest to the particle members of the particle set. For example, as in FIG. 1, a binding buffer is flowed into binding region 110 through a side channel and reservoir (not illustrated) fluidly coupled to channel 100, e.g., upstream from binding region 110. Such buffers include, but are not limited to, biological buffers that contain alcohol to enhance, e.g., the binding of proteins to a particle set. For example, Towbin's transfer buffer is optionally used in a binding region to aid binding of a component of interest to a particle set.

The binding buffer and/or the particle set is optionally introduced, e.g., from a particle well and/or buffer reservoir, into the binding region or channel, such as binding channel 110, after the mixture of components has been introduced into the channel. In other embodiments, a particle set comprising a component-binding moiety is positioned within the binding channel prior to introduction of the mixture of components. In other embodiments, the binding channel is a derivatized channel, e.g., a channel that comprises, e.g., on the walls of the channel, a component binding moiety. The mixture of components, e.g., proteins or carbohydrates, is incubated in the binding region, e.g., as the mixture flows through the region with the particle member types that comprise the particle set or with the component-binding moiety. Alternatively, the mixture of components remains in the binding region to incubate with the component binding moiety. Incubation times typically range from a few seconds to a few hours, e.g., less than about 10 seconds to about 30 minutes or more.

During the incubation time or while the mixture of compounds flows through the binding region, the component of interest in the mixture of components, e.g., a protein or carbohydrate, binds to the component-binding moiety or to the particle member type comprising the component-binding moiety.

For example, in one embodiment, a protein of interest adsorbs onto the particles which are stacked in a stacking region located in the binding region, e.g., with a barrier in the downstream end of the binding region to prevent the beads from flowing into other channels or channel regions of the device, e.g., into the separation region.

Adsorption refers to the adhesion of the components in a thin layer to the surface of the particles or beads of the invention with which they are in contact. Beads for use in adsorption of components include PVDF, nitrocellulose, and polyamides, such as nylon. Particle stacking and the type of beads or particles available to form particle sets are described further in U.S. patent application Ser. No. 09/510,626 filed Feb. 22, 2000, entitled "Manipulation of Microparticles In Microfluidic Systems," by Mehta et al.

Typically a particle set in the binding channel region or the binding channel region itself, e.g., the walls, comprises a component-binding moiety, e.g., an antibody or lectin that is specific to the component of interest, e.g., a protein or carbohydrate. As a component of interest flows across the particle set or through the binding channel region, the component of interest reacts with the component-binding moieties bound to the particles or the channel by binding specifically to the component-binding moiety. For example, a lectin or an antibody that specifically binds to a protein or carbohydrate of interest upon contact with the mixture of components in a binding channel binds to the component-binding moiety, thus capturing it so that all of the component of interest or a portion thereof remains bound in the binding region. The time for this binding to occur varies from a few seconds to a few hours. Preferably the binding occurs over a period that ranges from less than about 1 second to about 30 minutes or more. More preferably, the binding occurs over a period ranging from less than about 1 second to about 5 minutes or more. The time is optionally varied to adjust the sensitivity of detection.

Wash solutions, e.g., BSA solutions, detergent solutions, and the like, of varying stringency are optionally applied to the binding region or to the particle set within the binding region to remove any unbound components. Stringent wash solutions are optionally applied to remove, e.g., any components bound to the component-binding moiety in a non-specific manner. This works to reduce background levels in later detection of the component of interest.

By binding the component of interest in the binding channel, the component of interest is typically removed from the mixture of components, e.g., in whole (or in part if not all the component of interest is removed by binding to the component-binding moiety). The remaining unbound components in the mixture of components are then typically flowed from the binding region into a separation channel region, e.g., after the addition of a separation buffer and being heated in a heating zone. The mixture of components and the component of interest are thus individually detected, e.g., after separation, and identified, e.g., by comparing the retention time of the component of interest with the retention times of the individual components of the mixture when they were separated. Detection is typically achieved by detection of a label associated with each component in the mixture, e.g., an associative dye that selectively associates with, e.g., proteins or carbohydrates.

III. Separation of Components

After removing the component of interest or a portion thereof from the mixture of components in the binding region, the mixture of components is separated into its individual components, e.g., in a separation channel of a microfluidic device. After flowing the mixture through the binding channel region, the remaining mixture is flowed through a separation channel region, e.g., cross-injected into a separation channel or flowed through a separation region in the same channel as the binding region. For example, a mixture of components is optionally separated in separation region 230 of channel 260 of FIG. 2 or in separation region 130 of channel 100 of FIG. 1.

The separation channel or region typically comprises a separation matrix. When a sample is flowed through the separation matrix, the components are separated, e.g., based on physical or chemical properties, such as molecular weight or charge. The separation matrix optionally comprises a polymer, a gel, or a solution, etc.

Electrophoretic separation is the separation of substances achieved by applying an electric field to samples in a solution or gel. In its simplest form, it depends on the different velocities with which the substances or components move in the field. The velocities depend, e.g., on the charge and size of the substances.

Preferably, the separation channel region, such as separation channel region 130 in FIG. 1, is a polyacrylamide gel filled channel in which the mixture of components is electrophoretically separated based on charge/mass ratio or molecular weight. If the components are detected as they exit the separation region, e.g., in detection region 140, the components are optionally identified by their retention times.

Other gel electrophoretic media that are optionally placed in a separation channel or region of the invention include silica gels such as Davisil Silica, E. Merck Silica Gel, Sigma-Aldrich Silica Gel (all available from Supelco) in addition to a wide range of silica gels available for various purposes as described in the Aldrich catalogue/handbook (Aldrich Chemical Company, Milwaukee, Wis.). Preferred gel materials include agarose based gels, various forms of acrylamide based gels (reagents available from, e.g., Supelco, SIGMA, Aldrich, Sigma-Aldrich and many other sources), colloidal solutions, such as protein colloids (gelatins) and hydrated starches. For a review of electrophoretic separation techniques and polyacrylamide gels, see, e.g., The Encyclopedia of Molecular Biology, Kendrew (ed.) (1994); and, Gel Electrophoresis of Proteins: A Practical Approach, $2^{nd}$ edition Hames and Rickwood (eds.) IRL Press, Oxford England, (1990).

Other types of separation matrices are also optionally used and discussed in U.S. patent application Ser. No. 09/093,832 filed Jun. 8, 1998, entitled "Microfluidic Matrix Localizations Apparatus and Methods," by Mehta and Kopf-Sill. Alternate separation matrix media include low pressure chromatography media, such as non-ionic macroreticular and macroporous resins which adsorb and release components based upon hydrophilic or hydrophobic interactions, e.g., Amberchrom and Amberlite resins (available from Supelco), Dowex, and Duolite (all available from Supelco). Other optional media include affinity media for purification and separation, such as acrylic beads, agarose beads, cellulose, sepharose, or the like. In addition, a wide variety of resins and chromatography media are also available, e.g., from Supelco, Sigma, Aldrich, or the like, for example, biotin resins, dye resins, aluminas, carbopacks, etc. For a review of chromatography techniques and media, see, e.g., Affinity Chromatography—A Practical Approach, Dean et al., (eds.) IRL Press, Oxford (1985); and, Chromatographic Methods, $5^{th}$ Edition, Braithwaite et al., (1996).

In addition to separation matrices, detergents, such as SDS (sodium dodecylsulfate), are typically part of the separation environment in the separation channel. As explained in more detail below, such detergents act to, e.g., ensure that all components to be separated, e.g., proteins, are of the same charge (negative in the case of SDS) and thus migrate in the same direction. However, as also explained below in more detail, detergent concentrations above a certain point cause formation of micelles which can associate with dyes used in separation assays and thus cause high levels of background readings. The current invention cleverly includes embodiments that dilute, e.g., detergent levels, e.g., after the components and/or component(s) of interest pass through the separation channel, thereby avoiding and/or decreasing formation of detergent micelles. See, below.

For example, a protein sample that has been desalted and denatured in SDS is optionally electrophoresed in a linear polyacrylamide gel filled channel containing SDS to separate the proteins on the basis of molecular weight of the protein subunits. A detector is optionally positioned so that it detects proteins that are stained in the gel with a fluorescent protein stain, e.g., as they elute from separation region 130 into detection region 140 (as shown in FIG. 1). The retention time of the proteins as they are electrophoresed through the gel-filled channel is used, e.g., with markers, to measure the molecular weight of the proteins.

Heating Components Prior to Separation

In some embodiments, the mixture of components is heated prior to separation, e.g., in a heating zone as described above. For example, a mixture of components, e.g., minus any component of interest which remained behind in the binding channel region, is flowed through a heating region, such as region 120 in FIG. 1. The mixture is heated, e.g., to denature protein components prior to separation.

A channel region suitable for heating is often narrower or smaller in cross-section than other channel regions in the channel structure, as a smaller cross-section provides higher resistance in the fluid, which increases the temperature of the fluid as electric current passes through. Alternatively, the electric current is increased across the length of the channel by increased voltage, which also increases the amount of power dissipated into the fluid thus correspondingly increasing fluid temperature.

To selectively control the temperature of fluid at a region of the channel, a power supply applies voltage and/or current in one of many ways. For instance, a power supply can apply direct current (i.e., DC) or alternating current (i.e., AC), which passes through the channel and into a channel region which is smaller in cross-sectional area, thereby heating fluid in that region. This current is selectively adjusted in magnitude to complement any voltage or electric field that is applied to move fluid in and out of the region. AC current, voltage, and/or frequency can be adjusted, for example, to heat the fluid without substantially moving the fluid. Alternatively, a power supply can apply a pulse or impulse of current and/or voltage, which passes through the channel and into a channel region to heat fluid in the region. This pulse is selectively adjusted to complement any voltage or electric field that is applied to move fluid in and out of the region. Pulse width, shape, and/or intensity can be adjusted, for example, to heat the fluid substantially without moving the fluid or to heat the fluid while moving the fluid. Still further, the power supply can apply any combination of DC, AC, and pulse, depending upon the application. In practice, direct application of electric current to fluids in the microchannels of the invention results in extremely rapid and easily controlled changes in temperature.

A controller or computer, such as a personal computer, is optionally used to monitor the temperature of the fluid in the region of the channel where the fluid is heated. The controller or computer receives current and voltage information from, for example, the power supply, and identifies or detects temperature of fluid in the region of the channel. Depending upon the desired temperature of fluid in the region, the controller or computer adjusts voltage and/or current, etc. to meet the desired fluid temperature.

After heating in the heating zone, the mixture of components is typically separated to produce separated components, as described above, in a separation region, e.g., a polyacrylamide gel filled channel which separates components based on mass/charge ratios.

Post-Separation Dilution Prior to Detection

In some embodiments, buffer/detergent conditions in which the mixtures of components are separated (or in which the released component of interest is flowed through the separation channel) are altered after separation and during, or prior to, detection of the components. Such post-separation treatment is optionally used to improve detection, e.g., by reducing or eliminating adverse effects of detergent micelles. Detergent micelles, which are optionally used as described below in a separation buffer can interfere with detection. Therefore the micelle concentration is optionally reduced prior to detection.

Typically, a separation channel or channel region comprises a separation buffer, e.g., that is flowed into the separation channel region, e.g., from a buffer reservoir. Separation buffers typically comprise, e.g., a polymer matrix, a buffering agent, a detergent and a dye, e.g., an associative dye or a lipophilic dye. A separation buffer is typically flowed into the separation region and/or into a heating zone of the present devices and used to separate the mixture of components. For example, a side channel and reservoir (not illustrated), fluidly coupled to heating zone 220 and/or to separation region 230 in FIG. 2, are optionally used to introduce the mixture of components with the separation buffer.

A variety of polymer matrices are optionally used, e.g., as described herein, including cross-linked polymers and/or non-cross-linked polymers, e.g., linear polymers, as described herein. Typically, a non-cross-linked polymer is present in the separation buffer at a concentration of between about 0.01% and about 30% (w/v). Depending on the type of polymer used, the size of the separation channel, and the type of separation to be performed in the separation channel, the concentration may be different. Likewise, the molecular weight of the polymer can vary, e.g., depending on the resolution desired in the separation. Typically, the polymer ranges in molecular weight from about 1 kD to about 6,000 kD, with viscosities ranging from about 2 to about 1000 centipoise.

Typical buffering agents included in the separation buffers and separation channels of the present invention include, but are not limited to, tris, tris-glycine, HEPES, CAPS, MES, tricine, combinations thereof, and the like.

In addition, the separation buffer typically includes an associative dye moiety or other detectable labeling group, which associates with the components in the mixture of components that is to separated. This enables detection of the individual components as they flow through the separation buffer. As used herein, an "associative dye" or dye moiety refers to a detectable labeling compound or moiety, which associates with a class of molecules of interest, e.g., proteins or peptides, e.g., preferentially with respect to other molecules in a given mixture. For example, for protein and peptide characterization, lipophilic dyes are particularly useful because they associate with proteins and peptides in a solution preferentially to other components.

Examples of associative dyes for use in separation buffers in the separation channels of the present invention include, but are not limited to, fluorescent dyes, e.g., merocyanine dyes, such as those described in U.S. Pat. No. 5,616,502. Preferred dyes include some that are commercially available from Molecular Probes, Inc. (Eugene, Oreg.), such as Sypro Red™, Sypro Orange™, Syto 61™, and the like. Such dyes are typically intended for use in staining slab gels in which excess dye can be washed away to eliminate any adverse effects on SDS. However, as described in WO 00/46594, these dyes can also be used in capillary gel electrophoresis with surprising sensitivity and with little or no interference, e.g., with a post-separation dilution step as described below.

A detergent is also typically included in the separation buffer in a separation channel of the present invention. The detergent is used with the buffer, e.g., to ensure that all proteins/polypeptides in a sample migrate in the same direction under the electric field applied during electrophoresis of the sample mixture. For example, in typical protein separations, sodium dodecylsulfate (SDS) is included in the separation buffer. Proteins and/or polypeptides are coated with the detergent to provide each with a substantial negative charge. The negative charge causes all the components to migrate toward a cathode (i.e., of positive charge) under an electric current applied to a separation channel. In the sieving matrix or polymer, however, each component moves according to its molecular weight. For example, larger proteins move more slowly than smaller proteins, thereby allowing separation of a mixture of components.

In addition to SDS, a number of detergents are optionally used, e.g., anionic detergents. Alkyl sulfate, and alkyl sulfonate detergents, such as sodium octadecylsulfate, and sodium decylsulfate, are optionally used.

Detergents and polymers used in the separation buffers of the present invention are typically selected and provided at appropriate concentrations to optimize separation, e.g., to avoid interactions between buffer components that reduce separation efficiency, signal sensitivity, and the like. For example, the buffering agent and the detergent are typically provided at concentrations that optimize separation efficiency and minimize background signal and baseline signal irregularities.

However, the dye included in the separation buffer to detect the separated components can bind to detergent micelles and produce a substantial level of background signal during detection of the separated components, as well as giving rise to baseline irregularities. The concentration at which detergents begin to form micelles is termed the critical micelle concentration ("CMC"). See, e.g., Helenius et al., *Methods in Enzymol.* 56(63):734-749 (1979). See, also, PCT publication WO 00/46594 by Dubrow et al., "Methods, Devices, and Systems for Characterizing Proteins," published Aug. 10, 2000, for discussion of separation buffers and their optimization in microfluidic systems and determinations of CMC levels, which vary from detergent to detergent and with buffer strength.

The mixture of components is typically separated in an optimized separation buffer and or detergent concentration, which is optionally at, above, or below, the CMC. Once the sample components are separated, buffer conditions are optionally altered prior to detection to optimize the buffer for detection. For example, optimal detection conditions include, but are not limited to, detergent levels below the CMC. When lowered to below the CMC, detergent micelles disperse and the adverse effects of dye binding to micelles is reduced or eliminated. See, e.g., WO 00/46594, by Dubrow et al., published Aug. 10, 2000.

The conditions are typically altered using a dilution, e.g., adding a diluent to the separated components in the separation buffer prior to or during detection. By mixing the separated components with a diluent, the detergent in the buffer is diluted to be at or below the CMC. This is optionally done by altering the ratio of detergent and buffering agent or diluting the detergent level. The diluent thus adds to, maintains, or reduces the concentration of buffering agent while typically reducing the level of detergent. Alternatively, the diluent may maintain the level of detergent while reducing the concentration of buffering agent. In either instance, the desired goal is generally to eliminate detergent micelles at the time and point of detection. In other embodiments, the diluent added comprises a reagent that breaks up detergent micelles.

Example separation buffers used with this method include, but are not limited to, a buffer comprising a buffering agent at a concentration of about 10 to about 200 mM and a detergent concentration of about 0.01 to about 1.0% and typically above the CMC, e.g., about 0.05% above the CMC, and preferably about 0.1% above the CMC.

Detection of the separation components or released component of interest is preferably carried out in the absence of excessive micelles, which bind to the dye and can contribute to excessive background signals. Therefore, dilution of the separation buffer is optionally practiced to reduce the detergent concentration to a level below the CMC for that detergent used, e.g., less than about 0.1%. While this also typically dilutes the sample components to be detected, the substantial reduction in background as a result of micelle reduction enables easy detection at very low levels of sample.

Using the present microfluidic devices, the diluent is mixed with the separated components, e.g., post-separation. Therefore, a diluent is added into the microchannel comprising the separated components after they have eluted from the separation channel region and typically before they have entered into the detection region. A dilution channel is optionally used to add the diluent to the separated components or the released component of interest. The dilution channel, as used herein, comprises a channel through which a diluent is flowed. The diluent channel typically intersects, e.g., a main channel, downstream of the separation region and upstream from the detection region. Alternatively, the diluent channel intersects a channel in, or at, the detection region. The diluent or buffer material is flowed through the dilution channel and into a main channel or a detection region after sample components, e.g., separated components, have eluted from a separation region.

For example, in FIG. 3A, a mixture of components is flowed through binding region 310a, e.g., in a binding buffer. The component of interest binds to a component binding moiety in the binding channel region and remains bound in binding region 310a, e.g., while the remaining mixture of components continues to flow through channel 300a. As the mixture of components flows through intersection 370a, the portion of sample at the intersection is cross-injected into channel 360a, e.g., into a separation buffer comprising a detergent and an associative dye. The mixture of components then flows in a separation buffer through heating region 320a and separation region 330a, resulting in separated components. A diluent is then added to the separated components post-separation to dilute the detergent to avoid interference in the detection due to dye binding to detergent micelles. The diluent is optionally added via diluent channel 380a, after which the separated components, having been flowed through the separation region, are flowed into detection region 350a. The device in FIG. 3B works in a similar manner, e.g., using diluent channel 370b and reservoir 380b.

Therefore, the mixture of components, after passing through a binding channel region in which the component of interest is removed, is optionally mixed with a separation buffer, heated, separated into individual components, and diluted. A variety of channel configurations are optionally used to accomplish the various transitions and buffer changes. After such manipulations the separated components are detected, as described below, and the bound component of interest is released and analyzed.

IV. Release of Affinity Bound Compound of Interest

After being bound in the binding region by a component binding moiety, e.g., one attached to a particle set or derivatized on the channel walls, the component of interest is released from the binding region and flowed through the system in the same manner as the previously analyzed mixture of components. In other words, the component of interest is typically heated, separated, and detected after being released from the binding region. This typically occurs after the mixture of components has been separated into its various components.

For example, a released component of interest is optionally heated and mixed with a separation buffer, e.g., a buffer comprising a detergent and an associative dye. The released component is then flowed through a separation channel region, e.g., the same separation channel region in which the mixture of components was previously separated, and detected. The released component of interest is also optionally subjected to dilution, as described above, to reduce background dye signal. Detection of the separated components and the released component of interest typically results in two data sets, which can be superimposed, as described below, to identify the component of interest.

Release of the component of interest from the binding channel region typically comprises adjusting, e.g., the temperature or pH in the binding channel region to disfavor the binding of the component of interest to the component-binding moiety. The temperature is optionally adjusted, as described above in relation to heating zones, and/or the pH is changed (i.e., either increased or decreased), e.g., by introducing an acidic or basic reagent into the binding region. In other embodiments, one or more releasing agent is flowed through the binding channel region, e.g., to remove the component of interest from the component-binding moiety. For example, a competitive binding agent is optionally introduced into the binding region. In some embodiments, reagents such as detergents (e.g., SDS, Tween, etc.) are flowed through the binding channel region to release the component(s) of interest from the component-binding moiety.

The binding and releasing steps applied to the component of interest allow it to be separated from the overall mixture of components and individually detected, e.g., for separate detection and identification. Detection and analysis of the results are described in more detail below.

V. Detectors and Integrated Systems

After separating the mixture of components, and optionally diluting the detergent in the separation buffer, the separated components are flowed through a detection channel region, e.g., detection region 140 in FIG. 1. A detector positioned proximal to a detection region is used to detect the components as they flow through the region, e.g., past a detection window as described above. Likewise, the released component of interest is flowed past the detection region and detected. Detection typically occurs via, e.g., a label moiety attached to the components or a lipophilic dye associated with each component. The results from the detection of the mixture of components and the released component of interest are typically correlated to identify the component of interest or verify its presence in the mixture of components. In addition, the molecular weight of the components (as well as the component of interest) is optionally determined. A graphic display of the results is optionally in the form of linear intensity plots or virtual stained gel images, e.g., ones that are similar to standard western assay results. This allows the two sets of results to be overlaid or superimposed for identification of the component of interest.

Detectors for detecting the labeled components of the invention are well known to those of skill in the art. For example, where the label is a radioactive label, a scintillation counter or autoradiography is optionally used. Where the label is a fluorescent label moiety, it is detected by exciting the fluorochrome with the appropriate wavelength of light and detecting the resulting fluorescence. Other label moieties, include, but are not limited to, luminescent labels, color moieties, associative dyes, and the like. In some embodiments, the present methods comprise labeling the components of the mixture and the released component of interest, e.g., prior to or after separation. Such labeling is optionally performed in the microfluidic channels of the devices. Various detectors for use in the above methods are discussed in more detail below in the context of an integrated system.

Integrated Systems

Although the devices and systems specifically illustrated herein are generally described in terms of the performance of a few or one particular operation, it will be readily appreciated from this disclosure that the flexibility of these systems permits easy integration of additional operations into these devices. For example, the devices and systems described will optionally include structures, reagents and systems for performing virtually any number of operations both upstream and downstream from the operations specifically described herein. Such upstream operations include sample handling and preparation operations, e.g., cell separation, extraction, purification, amplification, cellular activation, labeling reactions, dilution, aliquotting, and the like. Similarly, downstream operations may include similar operations, including, e.g., separation of sample components, labeling of components, assays and detection operations, electrokinetic or pressure-based injection of components into contact with particle sets, or materials released from particle sets, or the like.

In the present invention, materials such as cells, proteins, nucleic acids, carbohydrates, or antibodies are optionally monitored and/or detected so that presence of a component of interest can be detected or an activity can be determined. Depending on the label signal measurements, decisions are optionally made regarding subsequent fluidic operations, e.g., whether to assay a particular component in detail to determine, e.g., kinetic information.

The systems described herein generally include microfluidic devices, as described above, in conjunction with additional instrumentation for controlling fluid transport, flow rate, and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing, and interpreting the data, and providing the data and interpretations in a readily accessible reporting format.

Fluid Direction System

A variety of controlling instrumentation is optionally utilized in conjunction wit the microfluidic devices described above, for controlling the transport and direction of fluidic materials and/or materials within the devices of the present invention, e.g., by pressure-based or electrokinetic control.

In the present system, the fluid direction system controls the transport, flow and/or movement of a sample through the microfluidic device. For example, the fluid direction system optionally directs the movement of the sample through the component separation region or channel, resulting in separated components. It optionally directs movement of a particle set and the separated components to a binding region, resulting in binding of the separated components to the plurality of particle member types. It also directs movement of the component-binding moiety to the binding region, resulting in binding of the component-binding moiety to the component of interest. In addition, movement of the particle set, separated components, and component-binding moiety to the detection region, where the component-binding moiety is detected, is also controlled by the fluid direction system.

For example, in many cases, fluid transport and direction are controlled in while or in part, using pressure based flow systems that incorporate external or internal pressure sources to drive fluid flow. Internal sources include microfabricated pumps, e.g., diaphragm pumps, thermal pumps, lamb wave pumps and the like that have been described in the art. See, e.g., U.S. Pat. Nos. 5,271,724, 5,277,556, and 5,375,979 and Published PCT Application Nos. WO 94/05414 and WO 97/02357. As noted above, the systems described herein can also utilize electrokinetic material direction and transport systems. Preferably, external pressure sources are used, and applied to ports at channel termini. These applied pressures, or vacuums, generate pressure differentials across the lengths of channels to drive fluid flow through them. In the interconnected channel networks described herein, differential flow rates on volumes are optionally accomplished by applying different pressures or vacuums at multiple ports, or preferably, by applying a single vacuum at a common waste port and configuring the various channels with appropriate resistance to yield desired flow rates. Example systems are described in U.S. Ser. No. 09/238,467 filed Jan. 28, 1999.

Typically, the controller systems are appropriately configured to receive or interface with a microfluidic device or system element as described herein. For example, the controller and/or detector, optionally includes a stage upon which the device of the invention is mounted to facilitate appropriate interfacing between the controller and/or detector and the device. Typically, the stage includes an appropriate mounting/alignment structural element, such as a nesting well, alignment pins and/or holes, asymmetric edge structures (to facilitate proper device alignment), and the like. Many such configurations are described in the references cited herein.

The controlling instrumentation discussed above is also used to provide for electrokinetic injection or withdrawal of material downstream of the region of interest to control an upstream flow rate. The same instrumentation and techniques described above are also utilized to inject a fluid into a downstream port to function as a flow control element.

Detectors

The devices herein optionally include signal detectors, e.g., which detect fluorescence, phosphorescence, radioactivity, pH, charge, absorbance, luminescence, temperature, magnetism, color, or the like. Fluorescent and chemiluminescent detection are especially preferred.

The detector(s) optionally monitors one or a plurality of signals from downstream of the separation region or channel in which a mixture of components was separated into individual components. Typically, the released component of interest is also flowed through the separation detected and detected as it elutes from the separation region or downstream of the separation region in order to compare its retention time to the other components of the mixture. For example, the detector optionally monitors an optical signal that corresponds to a labeled component, such as a labeled antibody located, e.g., in detection region 250 (in FIG. 2) or detection channel 140 (as shown in FIG. 1).

Example detectors include photo multiplier tubes, a CCD array, a scanning detector, a galvo-scanner or the like. Proteins, antibodies, nucleic acids, carbohydrates, or other components which emit a detectable signal are optionally flowed past the detector, or, alternatively, the detector can move relative to a channel region to determine protein position (or, the detector can simultaneously monitor a number of spatial positions corresponding to channel regions, e.g., as in a CCD array). For example, for particle member types that are stacked in a detection region, a detector can move relative to the stacked particles and detect them according to position within the stack.

The detector can include, or be operably linked to, a computer, e.g., which has software for converting detector signal information into assay result information, e.g., molecular weight based on retention time or elution time, identity of a protein, or the like.

Signals from arrays are optionally calibrated, e.g., by calibrating the microfluidic system by monitoring a signal from a known source.

A microfluidic system can also employ multiple different detection systems for monitoring the output of the system. Detection systems of the present invention are used to detect and monitor the materials in a particular channel region (or other detection region). Once detected, the flow rate and velocity of the materials in the channels are also optionally measured and controlled.

Examples of detection systems include optical sensors, temperature sensors, pressure sensors, pH sensors, conductivity sensors, and the like. Each of these types of sensors is readily incorporated into the microfluidic systems described herein. In these systems, such detectors are placed either within or adjacent to the microfluidic device or one or more channels, chambers or conduits of the device, such that the detector is within sensor communication with the device, channel, or chamber. The phrase "proximal," to a particular element or region, as used herein, generally refers to the placement of the detector in a position such that the detector is capable of detecting the property of the microfluidic device, a portion of the microfluidic device, or the contents of a portion of the microfluidic device, for which that detector was intended. For example, a pH sensor placed in sensory communication with a microscale channel is capable of determining the pH of a fluid disposed in that channel. Similarly, a temperature sensor placed in sensory communication with the body of a microfluidic device is capable of determining the temperature of the device itself. In addition to being used to detect components, e.g., downstream of a separation channel region, such sensors are optionally used to monitor a binding region, e.g., for desirable release conditions. For example, a pH sensor is optionally used to monitor the pH in a binding region to determine when a particular buffer or reagent, e.g., an acidic reagent, or how much of such a reagent should be introduced into the binding channel region to, e.g., release a bound component of interest.

Particularly preferred detection systems include optical detection systems for detecting an optical property of a material within the channels and/or chambers of the microfluidic devices that are incorporated into the microfluidic systems described herein. Such optical detection systems are typically placed adjacent to a microscale channel of a microfluidic device, and are in sensory communication with the channel via an optical detection window that is disposed across the channel or chamber of the device. Optical detection systems include systems that are capable of measuring the light emitted from material within the channel, the transmissivity or absorbance of the material, as well as the material's spectral characteristics. In preferred aspects, the detector measures an amount of light emitted from the material, such as a fluorescent or chemiluminescent material. As such, the detection system will typically include collection optics for gathering a light based signal transmitted through the detection window, and transmitting that signal to an appropriate light detector. Microscope objectives of varying power, field diameter, and focal length are readily utilized as at least a portion of this optical train. The light detectors are optionally photodiodes, avalanche photodiodes, photomultiplier tubes, diode arrays, or in some cases, imaging systems, such as charged coupled devices (CCDs) and the like. In preferred aspects, photodiodes are utilized, at least in part, as the light detectors. The detection system is typically coupled to a computer (described in greater detail below), via an analog to digital or digital to analog converter, for transmitting detected light data to the computer for analysis, storage and data manipulation.

In the case of fluorescent materials such as labeled cells, the detector typically includes a light source which produces light at an appropriate wavelength for activating the fluorescent material, as well as optics for directing the light source through the detection window to the material contained in the channel or chamber. The light source can be any number of light sources that provides an appropriate wavelength, including lasers, laser diodes and LEDs. Other light sources are required for other detection systems. For example, broad band light sources are typically used in light scattering/transmissivity detection schemes, and the like. Typically, light selection parameters are well known to those of skill in the art.

The detector can exist as a separate unit, but is preferably integrated with the controller system, into a single instrument. Integration of these functions into a single unit facilitates connection of these instruments with the computer (described below), by permitting the use of few or a single communication port(s) for transmitting information between the controller, the detector and the computer.

Computer

As noted above, either or both of the fluid direction system and/or the detection system are coupled to an appropriately programmed processor or computer which functions to instruct the operation of these instruments in accordance with preprogrammed or user input instructions, receive data and information from these instruments, and interpret, manipulate and report this information to a user. As such, the computer is typically appropriately coupled to one or both of these instruments (e.g., including an analog to digital or digital to analog converter as needed).

The computer typically includes appropriate software for receiving user instructions, either in the form of user input into set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. For example, the software or control system optionally directs the fluid direction system to transport a mixture of components through a binding channel region and then through a separation region. In addition, the mixture of components is optionally transported through a heating zone prior to the separation region and a dilution region after separation and prior to or during detection. The software also optionally directs release of the component of interest from the binding channel and through one or more of the remaining channel regions, e.g., the heating zone, separation region, dilution region, and detection region, and any other movement necessary to detect the component of interest.

The computer then receives the data from the one or more sensors/detectors included within the system, e.g., after detection of one or more components. The computer is used to interpret the data, either providing it in a user understood format, or using that data to initiate further controller instructions, in accordance with the programming, e.g., such as in monitoring and control of flow rates, temperatures, pH, applied voltages, and the like.

In the present invention, the computer typically includes software for the monitoring of materials in the channels. Additionally the software is optionally used to control the flow of materials through the channels. For example, monitoring of materials includes monitoring pH or detergent concentration. A control system or software is used to instruct the fluid direction system to introduce more or less buffer to achieve a desired pH or detergent concentration in a particular channel region.

In addition, the computer optionally includes software for deconvolution of the signal or signals from the detection system. For example, deconvolution optionally determines the molecular weight of the separated components and/or the released components of interest by determining the retention time of the components in the separation channel region. For example, comparison to standards is optionally used to determine molecular weight based on retention time or migration time through a separation region. Deconvolution of data is also used to analyze signals collected from the detection of the separated components and the released component of interest, e.g., to determine the identity of the component of interest. For example, detection of the separated components generates a first signal and detection of the released component of interest generates a second signal and deconvoluting comprises comparing the two signals to identify the component of interest, e.g., by retention time. A superposition of the two signals or the data sets generated therefrom is optionally used to identify the component of interest. For example, the data set produced from detection of the separated component is optionally presented in a gel (or a gel-like) format, e.g., a number of bands each corresponding to a different component, e.g., protein. When presented in the same manner, the data corresponding to the released component of interest yields a single band corresponding to the component of interest. The component of interest is thereby identified from the mixture.

Kits

Generally, the microfluidic devices described herein are optionally packaged to include reagents for performing the device's preferred function. For example, the kits optionally include any microfluidic device described along with assay components, reagents, sample materials, proteins, antibodies, detergents, dyes, particle sets, control materials, or the like. Such kits also typically include appropriate instructions for using the devices and reagents, and in cases where reagents are not predisposed in the devices themselves, with appropriate instructions for introducing the reagents into the channels and/or chambers of the device. In this latter case, these kits optionally include special ancillary devices for introducing materials into the microfluidic systems, e.g., appropriately configured syringes/pumps, or the like (in one preferred embodiment, the device itself comprises a pipettor element, such as an electropipettor for introducing material into channels and chambers within the device). In the former case, such kits typically include a microfluidic device with necessary reagents predisposed in the channels/chambers of the device. Generally, such reagents are provided in a stabilized form, so as to prevent degradation or other loss during prolonged storage, e.g., from leakage. A number of stabilizing processes are widely used for reagents that are to be stored, such as the inclusion of chemical stabilizers (e.g., enzymatic inhibitors, microbicides/bacteriostats, anticoagulants), the physical stabilization of the material, e.g., through immobilization on a solid support, entrapment in a matrix (e.g., a gel), lyophilization, or the like.

Kits also optionally include packaging materials or containers for holding microfluidic device, system or reagent elements.

The discussion above is generally applicable to the aspects and embodiments of the invention described in the claims. Moreover, modifications can be made to the method and apparatus described herein without departing from the spirit and scope of the invention as claimed, and the invention can be put to a number of different uses.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A method for detecting one or more component of interest in a microfluidic system, the method comprising the steps of:
   (i) flowing a mixture of components, which mixture of components comprises the one or more component of interest, through a binding channel region, which binding channel region comprises a component-binding moiety and which is upstream from a separation channel region, thereby binding at least a portion of the one or more component of interest to the component-binding moiety;
   (ii) flowing a remainder of the mixture of components through the separation channel region, resulting in one or more separated components, and detecting the one or more separated components;
   (iii) releasing the one or more component of interest from the component-binding moiety, resulting in one or more released component of interest; and,
   (iv) flowing the one or more released component of interest through the separation channel region and detecting the one or more released component of interest.

2. The method of claim 1, wherein the component of interest comprises a protein and the component-binding moiety comprises a protein-binding moiety.

3. The method of claim 1, wherein the component-binding moiety comprises an antibody specific to the component of interest.

4. The method of claim 1, wherein the component of interest comprises a carbohydrate and the component-binding moiety comprises a carbohydrate-binding moiety.

5. The method of claim 4, wherein the carbohydrate-binding moiety comprises a lectin specific to the carbohydrate.

6. The method of claim 1, wherein the component-binding moiety or the component of interest comprises a label moiety.

7. The method of claim 1, wherein the binding channel region comprises a derivatized channel.

8. The method of claim 1, wherein the binding channel region comprises one or more particle set, the particle set comprising a plurality of particle member types.

9. The method of claim 8, wherein the particle member types comprise a polymeric material, a silica material, a ceramic material, a glass material, a magnetic material, a metallic material, or an organic material.

10. The method of claim 8, wherein binding the component of interest to the component-binding moiety comprises adsorbing the component of interest onto one or more members of the particle set.

11. The method of claim 10, wherein the particle member types comprise a material selected from the group consisting of: PVDF, polyamide, nylon, and nitrocellulose.

12. The method of claim 8, wherein the particle member types are from about 0.1 mm to about 50 mm in diameter.

13. The method of claim 8, wherein one or more member of the plurality of particles comprises the component-binding moiety.

14. The method of claim 8 wherein the binding channel region comprises one or more particle set which is stacked in the binding region.

15. The method of claim 14 wherein the one or more particle set is fixed in place in the binding channel region.

16. The method of claim 1, comprising flowing the mixture of components through the binding channel region by applying pressure to the mixture of components.

17. The method of claim 1, comprising electrokinetically flowing the mixture of components through the separation channel region.

18. The method of claim 1, step (iv) comprising electrokinetically flowing the released component of interest through the separation channel region.

19. The method of claim 1, step (ii) comprising electrophoretically separating the mixture of components in a polymer or gel, which polymer or gel is disposed within the separation channel region.

20. The method of claim 1, step (ii) comprising electrophoretically separating the mixture of components in a polyacrylamide solution, matrix, or gel disposed within the separation channel region.

21. The method of claim 1, step (iii) comprising releasing the component of interest from the component-binding moiety by adjusting the temperature or pH in the binding channel region or by introducing one or more releasing reagent into the binding channel region.

22. The method of claim 1, further comprising contacting the mixture of components with a detergent and heating the mixture of components after step (i) and prior to step (ii).

23. The method of claim 1, further comprising contacting the released component of interest with a detergent and heating the released component of interest after step (iii) and prior to step (iv).

24. The method of claim 22 or claim 23, wherein heating comprises joule heating.

25. The method of claim 22 or claim 23, wherein the detergent comprises SDS.

26. The method of claim 1, wherein detecting the one or more separated components or detecting the released component of interest comprises optically detecting a luminescent, color, or fluorescent label moiety fixed to one or more of the separated components or the released component of interest.

27. The method of claim 1, the method further comprising labeling the mixture of components with a fluorescent label and detecting the separated components or the released component of interest by detecting the fluorescent label.

28. The method of claim 1, further comprising determining the molecular weight of the separated components or of the released component of interest by determining the retention time of the separated components or of the released component of interest in the separation channel region.

29. The method of claim 1, wherein detecting the one or more separated components produces a first signal and detecting the released component of interest produces a second signal and the method further comprises deconvoluting the first signal and the second signal to identify the separated components and the component of interest.

30. The method of claim 1, wherein detecting the one or more separated components produces a first data set and detecting the released component of interest produces a second data set.

31. The method of claim 30, further comprising superimposing the first data set and the second data set to identify the component of interest.

32. The method of claim 1, wherein the released component of interest has a migration time through the separation channel region, the method further comprising identifying the component of interest using the migration time.

33. The method of claim 1, wherein step (ii) comprises flowing the mixture of components through a separation channel region comprising a separation buffer, which separation buffer comprises a detergent and a dye moiety, and detecting the one or more separated components, the method further comprising diluting the detergent after flowing the mixture of components through the separation channel region and prior to or during the detecting of the one or more separated components.

34. The method of claim 33, wherein the separation buffer comprises a critical micelle concentration of the detergent or less.

35. The method of claim 33, wherein the dye comprises a lipophilic dye.

36. The method of claim 33, wherein detecting the one or more separated components comprises detecting the one or more separated components by detecting the dye, which dye associates with the one or more separated components.

37. The method of claim 33, wherein diluting the detergent comprises diluting the detergent to a level below a critical micelle concentration.

38. The method of claim 1 wherein the binding channel region and the separation channel region are located in the same channel of the microfluidic system.

39. The method of claim 1 wherein the binding channel region is located in a first channel of the microfluidic system which intersects with a second channel of the microfluidic system which contains the separation channel region.

40. The method of claim 1 wherein the binding channel region comprises a first region of increased or decreased channel depth or width with respect to a second region of a channel in which the binding channel region is located.

\* \* \* \* \*